United States Patent
Pawar et al.

(10) Patent No.: US 8,647,701 B2
(45) Date of Patent: *Feb. 11, 2014

(54) DIFFUSION-HARDENED MEDICAL IMPLANT

(75) Inventors: Vivek Pawar, Germantown, TN (US); Shilesh C. Jani, Germantown, TN (US); Carolyn Weaver, San Francisco, CA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/170,084

(22) Filed: Jun. 27, 2011

(65) Prior Publication Data

US 2011/0320007 A1 Dec. 29, 2011

Related U.S. Application Data

(60) Continuation of application No. 12/244,492, filed on Oct. 2, 2008, now Pat. No. 7,968,209, which is a division of application No. 11/558,756, filed on Nov. 10, 2006, now Pat. No. 7,550,209.

(60) Provisional application No. 60/705,557, filed on Dec. 15, 2005.

(51) Int. Cl.
| | |
|---|---|
| C23C 22/00 | (2006.01) |
| C23C 8/10 | (2006.01) |
| A61F 2/28 | (2006.01) |
| B05D 3/02 | (2006.01) |
| B05D 3/12 | (2006.01) |

(52) U.S. Cl.
USPC .......... 427/2.26; 148/277; 148/206; 148/672; 148/281; 623/23.53

(58) Field of Classification Search
USPC ......... 427/2.1, 2.26, 2.29; 148/277, 269, 284, 148/281

See application file for complete search history.

(56) References Cited

U.S. PATENT DOCUMENTS

| | | |
|---|---|---|
| 2,987,352 A | 6/1961 | Watson |
| 3,597,664 A | 8/1971 | Villani |

(Continued)

FOREIGN PATENT DOCUMENTS

| | | |
|---|---|---|
| EP | 0555038 | 8/1993 |
| EP | 0 608 997 | 8/1994 |

(Continued)

OTHER PUBLICATIONS

Hobbs et al., "Oxidation Microstructures and Interfaces in the Oxidized Zirconium Knee", International Journal of Applied Ceramic Technology, 2005, 221-246, vol. 2(3).

(Continued)

*Primary Examiner* — Cachet Sellman
(74) *Attorney, Agent, or Firm* — David A. Chambers

(57) ABSTRACT

Methods of making surface hardened medical implants comprising providing a biocompatible alloy with a surface comprising an oxide or nitride layer, diffusing at least a portion of the respective oxygen or nitrogen from the oxide or nitride layer the substrate for a period of time to form a diffusion hardened zone of desired thickness. The period of time is based at least on (1) the diffusivity of a diffusing specie in the oxide or nitride layer, (2) a desired hardness profile of at least a portion of said implant defined by a function selected from the group consisting of: an error function, an exponential function, a near uniform distribution function, and any sequential combination thereof, or (3) a desired thickness of said oxide or nitride layer to be retained.

12 Claims, 18 Drawing Sheets

(56) References Cited

U.S. PATENT DOCUMENTS

| | | | |
|---|---|---|---|
| 3,615,885 A | 10/1971 | Watson et al. | |
| 4,145,764 A | 3/1979 | Suzuki et al. | |
| 5,037,438 A | 8/1991 | Davidson | |
| 5,152,794 A | 10/1992 | Davidson | |
| 5,169,597 A | 12/1992 | Davidson et al. | |
| 5,180,394 A | 1/1993 | Davidson | |
| 5,211,663 A | 5/1993 | Kovacs et al. | |
| 5,265,137 A | 11/1993 | Busch | |
| 5,282,861 A | 2/1994 | Kaplan | |
| 5,316,594 A | 5/1994 | Kemp | |
| 5,338,771 A | 8/1994 | Neumann et al. | |
| 5,370,694 A | 12/1994 | Davidson | |
| 5,372,660 A * | 12/1994 | Davidson et al. | 148/421 |
| 5,399,207 A * | 3/1995 | Kemp | 148/209 |
| 5,405,394 A | 4/1995 | Davidson | |
| 5,415,704 A | 5/1995 | Davidson | |
| 5,496,359 A | 3/1996 | Davidson | |
| 5,549,700 A | 8/1996 | Graham et al. | |
| 5,562,730 A | 10/1996 | Davidson | |
| 5,588,443 A | 12/1996 | Davidson | |
| 5,611,347 A | 3/1997 | Davidson | |
| 5,716,400 A | 2/1998 | Davidson | |
| 5,782,910 A | 7/1998 | Davidson | |
| 5,830,396 A | 11/1998 | Higgins et al. | |
| 5,868,879 A | 2/1999 | Amick et al. | |
| 6,043,437 A | 3/2000 | Schulman et al. | |
| 6,059,830 A | 5/2000 | Lippincott, III et al. | |
| 6,063,442 A | 5/2000 | Cohen et al. | |
| 6,087,553 A | 7/2000 | Cohen et al. | |
| 6,146,686 A | 11/2000 | Leitao | |
| 6,207,218 B1 | 3/2001 | Layrolle et al. | |
| 6,447,550 B1 | 9/2002 | Hunter et al. | |
| 6,472,122 B1 | 10/2002 | Schulman et al. | |
| 6,585,772 B2 | 7/2003 | Hunter et al. | |
| 6,652,586 B2 | 11/2003 | Hunter et al. | |
| 6,726,725 B2 | 4/2004 | Hunter et al. | |
| 6,833,197 B1 * | 12/2004 | Morton et al. | 428/472.1 |
| 6,869,701 B1 * | 3/2005 | Aita et al. | 428/698 |
| 6,881,229 B2 | 4/2005 | Khandkar et al. | |
| 7,048,767 B2 | 5/2006 | Namavar | |
| 7,070,623 B2 | 7/2006 | Hunter et al. | |
| 7,473,278 B2 | 1/2009 | Hunter et al. | |
| 2002/0042656 A1 | 4/2002 | Hunter et al. | |
| 2003/0033020 A1 * | 2/2003 | Hunter et al. | 623/23.54 |
| 2003/0125808 A1 | 7/2003 | Hunter et al. | |
| 2003/0153979 A1 | 8/2003 | Hughes et al. | |
| 2003/0153981 A1 | 8/2003 | Wang et al. | |
| 2003/0220699 A1 | 11/2003 | Hunter et al. | |
| 2004/0122524 A1 | 6/2004 | Hunter et al. | |
| 2005/0033442 A1 | 2/2005 | Fisher et al. | |
| 2006/0052880 A1 | 3/2006 | Brosnahan et al. | |
| 2006/0058888 A1 * | 3/2006 | Hunter et al. | 623/23.39 |
| 2006/0169364 A1 * | 8/2006 | Trotzschel et al. | 148/269 |
| 2007/0137734 A1 | 6/2007 | Pawar et al. | |

FOREIGN PATENT DOCUMENTS

| | | |
|---|---|---|
| JP | 60-036654 | 2/1985 |
| WO | WO-9402083 | 2/1994 |
| WO | WO-9904055 | 1/1999 |

OTHER PUBLICATIONS

International Search Report, issued Sep. 24, 2007 re International Application No. PCT/US06/43838. Published Dec. 21, 2007.

Long et al., "Nano-Hardness Measurements of Oxidized Zr-2.5Nb and Various Orthopaedic Materials", 24th Annual Meeting of the Society for Biomaterials, Apr. 22-26, 1998 San Diego, California, USA.

Sprague et al., "Mechanical Behavior of Zirconia, Alumina, and Oxidizen, Zirconium Modular Heads", ISTA, 2003, vol. 2.

Takamura, "Surface Hardening of Titanium by Oxygen", Trans. JIM, 1962, 10-14, vol. 3.

Treco, "Solution and Diffusion of Corrosion Oxide Film in Zircaloy", J. Electrochem. Soc., 1962, 208-211, vol. 109.

Written Opinion issued Sep. 24, 2007 re International Application No. PCT/US06/43838. Published Jun. 15, 2008.

Horton et al., "Biomedical Potential of a Zirconium-Based Bulk Metallic Glass," found at http://www.oml.gov/webworks/cppr/y2001/pres/, Article No. 116372, 2003.

Study of Oxidation Behaviour of Zr-based Bulk Amorphous Alloy Zr65Cu17-5Ni10A17-5 by thermogravimetric analyser; Bull. Mater. Sci., vol. 24, No. 3, Jun. 2001, pp. 281-283. O Indian Academy of Sciences.

Telford, "The case for bulk metallic glass", Materials Today, 7(3): 36-43, 2004.

Triwikantoro et al., "Oxidation of Zr-based Metallic Glasses in Air," Journal of Non-Crystalline Solids, 719-723, 1999.

Tuffias, "Novel Material Spinal Implants," BMDO Technologies for Biomedical Applications Chapter 3 Intervention Technologies Section A—Implants.

IDS filed on Dec. 2, 2010 for U.S. Appl. No. 11/740,006.

IDS filed on Apr. 25, 2007 for U.S. Appl. No. 11/740,006.

* cited by examiner

DIFFUSION-HARDENED MEDICAL IMPLANT

CROSS-REFERENCE TO RELATED APPLICATIONS

This application claims priority to, and is a continuation application of U.S. application Ser. No. 12/244,492, now U.S. Pat. No. 7,968,209, filed on Oct. 2, 2008, which claims priority to U.S. application Ser. No. 11/558,756, filed on Nov. 10, 2006, now U.S. Pat. No. 7,550,209, which claims priority to U.S. provisional application serial No. 60/750,557, filed on Dec. 15, 2005, the disclosures of which are incorporated herein by reference.

TECHNICAL FIELD

The present invention relates to a new composition of diffusion-hardened oxidized zirconium. The new composition has application, for example, in articulating and non-articulating surfaces of medical implants. The present invention also relates to orthopedic implants comprising the new composition, methods of making the new composition, and methods of making medical implants comprising the new composition. While the present implant composition is useful in hard-on-soft applications (e.g., a medical implant component of the present invention articulating against polyethylene), the present invention also encompasses the use of this new medical implant composition in hard-on-hard applications (e.g., the present composition articulating against itself or against other hard materials and ceramics) in a hip, knee, spinal, or other implant.

BACKGROUND OF THE INVENTION

Medical implant materials, in particular orthopedic implant materials, must combine high strength, corrosion resistance and tissue compatibility. The longevity of the implant is of prime importance especially if the recipient of the implant is relatively young because it is desirable that the implant function for the complete lifetime of a patient. Because certain metal alloys have the required mechanical strength and biocompatibility, they are ideal candidates for the fabrication of prostheses. These alloys include 316L stainless steel, chrome-cobalt-molybdenum alloys (Co—Cr), titanium alloys and more recently zirconium alloys which have proven to be the most suitable materials for the fabrication of load-bearing and non-load bearing prostheses.

To this end, oxidized zirconium orthopedic implants have been shown to reduce polyethylene wear significantly. The use of diffusion-hardened oxide surfaces such as oxidized zirconium in orthopedic applications was first demonstrated by Davidson in U.S. Pat. No. 5,037,438. Previous attempts have been made to produce oxidized zirconium coatings on zirconium parts for the purpose of increasing their abrasion resistance. One such process is disclosed in U.S. Pat. No. 3,615,885 to Watson which discloses a procedure for developing thick (up to 0.23 mm) oxide layers on Zircaloy 2 and Zircaloy 4. However, this procedure results in significant dimensional changes especially for parts having a thickness below about 5 mm, and the oxide film produced does not exhibit especially high abrasion resistance.

U.S. Pat. No. 2,987,352 to Watson discloses a method of producing a blue-black oxide coating on zirconium alloy parts for the purpose of increasing their abrasion resistance. Both U.S. Pat. No. 2,987,352 and U.S. Pat. No. 3,615,885 produce a zirconium oxide coating on zirconium alloy by means of air oxidation. U.S. Pat. No. 3,615,885 continues the air oxidation long enough to produce a beige coating of greater thickness than the blue-black coating of U.S. Pat. No. 2,987,352. This beige coating does not have the wear resistance of the blue-black coating and is thus not applicable to many components where there are two work faces in close proximity. The beige coating wears down more quickly than the blue-black oxide coating with the resulting formation of oxidized zirconium particles and the loss of the integrity of the oxidized zirconium surface. With the loss of the oxide surface the zirconium metal is then exposed to its environment and can lead to transport of zirconium ions into the adjacent environment.

The blue-black coatings have a thickness which is less than that of the beige coating although the hardness of the blue-black coating is higher than that of the beige coating. This harder blue-black oxide coating lends itself better to surfaces such as prosthetic devices. Although the blue-black coating is more abrasion resistant than the beige coating it is a relatively thin coating. It is therefore desirable to produce new and improved compositions that maintain the desirable properties of the blue-black coatings of the prior art (for example, increased abrasion resistance).

As discussed above, U.S. Pat. No. 5,037,438 to Davidson discloses a method of producing zirconium alloy prostheses with a oxidized zirconium surface. U.S. Pat. No. 2,987,352 to Watson discloses a method of producing zirconium bearings with a oxidized zirconium surface. The oxide coating produced is not always uniform in thickness and the non-uniformity reduces the integrity of the bonding between the zirconium alloy and the oxide layer and the integrity of the bonding within the oxide layer. Both U.S. Pat. No. 2,987,352 and U.S. Pat. No. 5,037,438 are incorporated by reference as though fully set forth herein.

In U.S. Pat. Nos. 6,447,550; 6,585,772 and pending U.S. application Ser. No. 10/942,464, Hunter, et al. describe methods for obtaining an oxidized zirconium coating of uniform thickness. Hunter teaches that such is obtained by applying pre-oxidation treatment techniques and by manipulation of substrate microstructure. The use of uniform thickness oxide layer results in increased resistance to corrosion by the action of the body fluids as well as other benefits and is biocompatible and stable over the lifetime of the recipient. U.S. Pat. Nos. 6,447,550; 6,585,772 and pending U.S. application Ser. No. 10/942,464 are incorporated by reference as though fully set forth herein.

The oxidized zirconium surfaces of Davidson and Hunter (henceforth referred as Davidson-type oxidized zirconium composition), while having relatively thick ceramic oxide or nitride layers, did not exhibit thick diffusion hardened zones below the ceramic oxide or nitride. The diffusion hardened zones of Davidson-type oxidized zirconium compositions had thicknesses of at most 1.5-2 microns and typically less depending upon the conditions used to produce the composition. FIG. 1 shows the nano-hardness profile of Davidson-type oxidized zirconium composition (FIG. 1 is taken from M. Long, L. Reister and G. Hunter, Proc. 24$^{th}$ Annual Meeting of the Society For Biomaterials, Apr. 22-26, 1998, San Diego, Calif., USA). The diffusion zone of the Davidson-type oxidized zirconium is between 1.5 to 2 microns. The oxide is approximately 5 microns, hence the totality of the hardened zone in the Davidson oxide is approximately 7 microns. While the resulting compositions of Davidson and Hunter exhibited high wear resistance in comparison to those compositions available in the prior art, there is still room for improvement.

The significant reduction in wear of polyethylene against oxidized surfaces is attributed to the ceramic nature of the oxide. The oxidized zirconium implant typically has a 5 to 6 micron thick ceramic surface (zirconium oxide) that is formed by a thermally driven diffusion process in air. Beneath the zirconium oxide is a hard, oxygen-rich diffusion layer of approximately 1.5 to 2 microns. The totality of hardened zones (oxide plus diffusion hardened alloy) render the implant resistant to microscopic abrasion (for example, from third bodies such as bone cement, bone chips, metal debris, etc.) and slightly less resistant to macroscopic impact (surgical instrumentation and from dislocation/subluxation contact with metallic acetabular shells). The smaller hardening depth of these implants renders them less than optimal for hard-on-hard applications. In a hard-on-hard application such as in a hip joint, the material articulates against itself or another hardened or non-hardened metal instead of polyethylene. The wear rates in such types of implants could be as high as 1 micron per year. With the totality of the hardened zone (oxide and diffusion zone) having a thickness of less than 7 microns, Davidson-type oxidized zirconium implants, although representing the state-of-the-art when originally introduced and still quite useful, have room for improvement in such applications. Hunter et al (U.S. Pat. No. 6,726,725) teaches such hard-on-hard applications for Davidson-type oxidized zirconium components. Hunter '725 teaches that the oxide thickness can be increased up to 20 microns for such applications. But as will be shown herein, Davidson-type oxide compositions having such thicknesses, although highly wear-resistant, can have significant number of oxide layer defects. Such defects can lead to localized spalling of the oxide. Also, in the Davidson-type composition below the oxide, there is a relatively small diffusion hardened zone. Thus, while the Davidson-type compositions exhibited superior wear resistance compared to many conventional materials, there is always room for improvement.

Currently, there are two primary types of hard-on-hard hip implants that are available commercially, namely metal-on-metal and ceramic-on-ceramic. The current standard material of metal-on-metal implants is high carbon Co—Cr alloy. The major concern with the metal-on-metal implant is the metal ion release from the joint and its unknown effects on the physiology of the human body. The advantage of metal-on-metal implants is that they can be used in larger sizes. The larger size of the implant allows greater range of motion. The metal-on-metal implants have also been shown to be useful for resurfacing type of application where conservation of bone is desired. In such larger joints, the conventional or cross-linked polyethylene is not preferred and metal-on-metal may be the only choice available. The larger size requires polyethylene liner to be thinner. A thinner liner may not be mechanically strong, may creep more or may lead to increased wear and osteolysis and eventually failure of the implant.

The other commonly used hard-on-hard implant material is ceramic-on-ceramic. The current standard material of ceramic-on-ceramic implants is alumina. Metal ion release is typically not a concern for these implants. But due to limited toughness and the brittle nature of ceramics, it is difficult to make these implants in larger sizes. The ceramic components have finite probability of fracture thus leading to a potential joint failure and complications associated with the fracture of a joint.

It has been an object of much of the prior art to reduce the metal ion release and minimize the fracture risk by combining metal and ceramic components. Fisher et al (U.S. Patent Application 2005/0033442) and Khandkar et al. (U.S. Pat. No. 6,881,229) teach using a metal-on-ceramic articulation. Fisher et al teach that the difference in hardness between the metallic component and the ceramic component to be at least 4000 MPa. Khandkar et. al. specifically teach use of silicon nitride ceramic components for articulating against the metallic component. In both instances the objective is to lower the wear of mating couples. But in both instances, the fracture risk of ceramic is still significant. The object of the present invention is to eliminate the risk of fracture along with metal ion release. It is eliminated by using a metallic component with ceramic surface and diffusion hardened zone below the ceramic surface. As mentioned in the details of the invention, diffusion hardened composition of present invention provides a solution to the above described problems pertaining to hard-on-hard bearings made from Davidson-type oxidized zirconium, high carbon CoCr (cobalt-chromium) and alumina. In one aspect of invention, the invented composition is applicable in knee joints and in spinal joints where hard-on-hard articulation is desired.

Unlike the Davidson-type oxidized zirconium, the oxidized zirconium composition disclosed herein is significantly less susceptible to damage caused by dislocation and subluxation. Thus, while the application of diffusion-hardened oxide layers such as Davidson-type oxidized zirconium to orthopedic implants represented a great improvement in the art of implant materials, resulting in substantial improvements in abrasion resistance and service life, the new compositions of the present invention represent improvements over the Davidson-type compositions.

Production of a diffusion hardened zone in zirconium (and its alloys) and titanium (and its alloys) has been disclosed previously. One of the approach suggested by Kemp (U.S. Pat. No. 5,399,207) is to oxidize a zirconium alloy in a temperature range of 426° C. (800° F.) to 871° C. (1600° F.) for two hours or more. The approach of Kemp is to run the process longer so that oxygen diffuses farther into the substrate while the oxidation is taking place. The major disadvantage of this approach is higher temperature and prolonged time is required to form a thicker diffusion zone. The higher temperature and prolonged time can lead to microstructural changes in the substrate and to a defective oxide that comprises substantial amounts of cracks and pores. Kemp teaches the application of its method on a Zircadyne 702 substrate. Following the teachings of Kemp, Zircadyne 702 and medical grade Zr-2.5Nb (ASTM F2384) were oxidized at 800° C. The oxide thickness of Zircadyne-702 samples was 10 to 12 micron whereas that of Zr-2.5Nb was approximately 20 microns (FIGS. 2(a) and 2(b)). The diffusion hardened zone on both samples was approximately 25 microns (FIG. 2(c)). The oxide of both samples showed substantial defects in the form of cracks and pores.

In another approach, Davidson (U.S. Pat. No. 5,372,660) teaches oxidizing Ti alloy that contains Zr. The presence of Zr in Ti leads to formation of an oxide and a thicker diffusion zone. Following the teachings of Davidson an alloy of Ti—Zr—Nb (55% Ti w/w, 35% Zr w/w and 10% Nb w/w) and medical grade Zr-2.5 Nb were oxidized in air. The alloy samples were oxidized at 635° C. for 6 hours. FIG. 3 shows metallographic images showing the oxide and diffusion hardened zone. The oxide of both Ti—Zr—Nb and Zr-2.5Nb is cracked. The oxide of Ti—Zr—Nb appears to separate from the substrate at several locations. FIG. 3 (c) shows microhardness of diffusion hardened zone. The Ti—Zr—Nb alloy shows approximately 10 to 15 micron thick diffusion hardened zone. The diffusion hardened zone of Zr-2.5Nb is less than 5 microns. Thus following the teachings of Kemp and Davidson, a significant depth of hardening could be obtained but at the cost of substantial defects in the resulting oxide. Kemp teaches a prolonged treatment at elevated temperatures, whereas Davidson teaches changing the chemistry of the alloy to form a thicker diffusion hardened zone. But in both cases the oxide formed is full of defects. Such type of defects in the oxide can compromise integrity of the oxide and may lead to localized spalling. One of the compositions disclosed herein comprises a thick diffusion zone along with a substantially defect-free oxide. The oxide disclosed herein has additional distinctions over the prior art that will be disclosed further in the details herein. The Davidson-type and Kemp-type oxidized zirconium product is an oxide that is predominantly single phase. The oxide of the present invention comprises a secondary phase that is ceramic or oxygen-rich metal. Embodiments of the diffusion hardened zone of the present invention have a layered structure and a preferred hardness profile.

Another approach to produce a diffusion hardened metallic zone is basically one of forming an oxide on the surface of the article by treatment in an oxygen-rich environment, followed by heat treating the article in an oxygen-deficient environment. One of the approaches provided by Takamura (Trans JIM, vol. 3, 1962, p. 10) has been to oxidize a titanium sample followed by treating it in argon gas (i.e., an oxygen deficient environment with a low partial pressure of oxygen). This apparently allows oxygen to diffuse in the substrate and form a thick diffusion zone. Presence of oxygen in the diffusion zone leads to hardening. Another approach suggested by Dong et al (U.S. Pat. No. 6,833,197) is to use vacuum or an inert gas mixture to achieve an oxygen-deficient environment, thereby achieving the diffusion-hardening after oxidation. The preferred temperature specified by both Takamura and Dong et al for oxidation is 850° C. and that for diffusion hardening (vacuum treatment) is 850° C. Dong et al suggest this methodology for titanium and zirconium and titanium/zirconium alloys. One of the problems with these methods, particularly for zirconium alloys, is that the oxidation and diffusion hardening temperatures are significantly high and can lead to thick and cracked (defective) oxide as well as cracks in the substrates after diffusion hardening. Dong demonstrates its method using titanium alloys; no examples for zirconium/niobium-based or titanium/zirconium/niobium-based alloys have been shown.

Both Takamura and Dong et. al. recommend a preferred temperature of oxidation and inert gas/vacuum treatment of 850° C. Following their teachings, samples of Ti-6Al-4V and medical grade Zr-2.5Nb were oxidized at 850° C. for 0.3 hr in air. FIGS. 4(a) and 4(b) show metallographic images after oxidation. The oxide on the Ti-6Al-4V is less than 1 micron thick. The oxide does not seem to adhere well to the substrate. The oxide on Zr-2.5Nb is approximately 12 microns thick and it is cracked. Following the teachings of Dong, both samples were subjected to vacuum treatment under pressure of $10^{-4}$ ton and at 850° C. for 22 hours. FIGS. 4(c) and 4(d) show metallographic images after vacuum treatment. In both samples, oxide has dissolved into the substrate. There are no visible cracks in Ti-6Al-4V sample. The crack is still present on the surface of the Zr-2.5Nb sample. The crack appears to have propagated inside the substrate during the vacuum treatment. These types of cracks on the surface can significantly reduce fatigue strength of the alloy. The new composition and method of the present invention overcomes these deficiencies.

In order to further demonstrate the difference in the behavior between Ti and Zr alloys, samples of Ti-6Al-4V and Zr-2.5Nb were oxidized at a lower temperature (600° C. for 75 minutes). These samples were then treated under vacuum ($<10^{-4}$ ton) at 685° C. for 10 hours. As will be disclosed further herein, the treatment was carried out in such a way that oxide is partially retained on the Zr-2.5Nb substrate. FIGS. 5(a) and 5(b) show metallographic images of the oxide formed on Ti-6Al-4V and Zr-2.5Nb samples. The oxide on Ti-6Al-4V is less than 0.1 micron whereas it is approximately 3 micron on Zr sample. No cracks are visible on both samples. After vacuum diffusion hardening, oxide on a Ti-6Al-4V sample is completely dissolved whereas approximately 1 micron oxide is retained on a Zr-2.5Nb sample (FIGS. 5(c) and 5(d)). FIG. 5(e) shows the hardness profile of the diffusion zone. Oxygen diffused almost entirely through the Ti alloy sample and thus produced a negligibly small depth of hardening whereas it did produce a significant depth of hardening in Zr alloy. This example further illustrates the differences in Zr and Ti alloys in the Dong process. It is evident from these examples that the range of temperatures that may work for Zr alloys may not be optimal for Ti alloys and vice versa. Dong also teaches a sigmoid shaped hardness profile of the diffusion hardened metallic zone. The sigmoid shaped diffusion hardened zone profile requires almost complete dissolution of the oxide in the substrate. The inventors of the present invention have found that this is not necessary. The inventors have found that in one aspect of this invention, it is advantageous to retain the oxide on the surface during this process. This is accomplished by careful selection of temperature and time for oxidation and subsequent diffusion hardening. Dong does not teach or suggest retention of the oxide on the surface of the sample at the end of the vacuum treatment and obtaining different types of oxygen concentration or hardness profiles other than a sigmoid profile when the oxide is almost completely dissolved.

In another approach of the prior art, Treco (R. Treco, J. Electrochem. Soc., Vol. 109, p. 208, 1962) used vacuum annealing method to completely dissolve the oxide formed on Zircalloy-2 after corrosion testing. The objective of Treco's work was to eliminate the oxide by vacuum annealing and the resultant diffusion zone by acid pickling. Treco neither discloses advantage of retaining the oxide during diffusion process nor discloses an application where such surfaces could be used. Finally, both Dong and Treco do not disclose use of such a technique to form a ceramic oxide and diffusion hardened zone to make a damage resistant medical implant.

The inventors have found that the damage (i.e., wear) resistance of diffusion hardened medical implant compositions can be improved by increasing the thickness of totality of the hardened zones. The resulting diffusion hardened medical implant compositions are new and not disclosed or suggested in the prior art. The desired totality of hardened zones can be achieved by varying the thicknesses of the ceramic oxide (or nitride, or mixed oxide/nitride) and the underlying diffusion hardened zone(s). Additionally, an increase in the thickness of the diffusion hardened zone imparts additional wear resistance desired in hard-on-hard articulation. A thicker diffusion hardened zone exhibits a layered structure in which the concentration of the diffusion hardening species varies with depth. Careful consideration needs to be applied in selecting the temperature and time of oxidation and diffusion hardening to achieve the desired totality of the hardened zones, while retaining (or enhancing) most of the mechanical, and electrochemical properties of the articles. Furthermore, the proper conditions for the processes of manufacture of such compositions are related to the alloy system under consideration. Such hardened alloys are suitable for articulation against soft polymers (such as ultra high molecular weight polyethylene (UHMWPE), cross-linked polyethylene (XLPE), polyurethane, etc and in hard-on-hard bearing applications against like hardened alloys, against CoCr alloys, ceramics (alumina, silicon nitride, silicon carbide, zirconia, etc), other hard materials such as diamond, diamond-like carbon and ceramic coatings (metal-oxides, metal-nitrides, metal-carbides and diamond), etc.

All of the above-referenced U.S. patents and published U.S. patent applications are incorporated by reference as though fully described herein.

BRIEF SUMMARY OF THE INVENTION

In one aspect of the present invention there is a medical implant comprising: a substrate comprising zirconium or zirconium alloy; a diffusion hardened zone in contact with said substrate, said diffusion hardened zone comprising zirconium or zirconium alloy and a diffusion hardening species, said diffusion hardened zone having a thickness of greater than 2 microns; and, a substantially defect-free ceramic layer in contact with said diffusion hardened zone and comprising a surface of said medical implant, said ceramic layer ranging in thickness from 0.1 to 25 microns; and, wherein the total thickness of the ceramic layer and the diffusion hardened zone is 5 microns or greater. In some embodiments, the ceramic layer comprises a secondary phase, and the diffusion hardened zone has a layered structure comprising at least two distinct layers under metallographic analysis, the layered structure characterized by: a first layer directly below the ceramic layer, wherein the first layer is predominantly alpha phase zirconium; an interface between the first layer and the ceramic layer; and; a second layer directly below the first layer. In some embodiments, the substrate further comprises titanium, tantalum, hafnium, niobium, and any combination thereof. In some embodiments, the diffusion hardening species is selected from the group consisting of oxygen, nitrogen, boron, carbon, and any combination thereof. Preferably, the diffusion hardening species comprises oxygen. In some embodiments, the diffusion hardened zone has a concentration of oxygen which decreases in the direction of the substrate, said decrease of oxygen concentration being defined by a function selected from the group consisting of an error function, an exponential function, a near uniform distribution function, and any sequential combination thereof. In some embodiments, the ceramic oxide has monoclinic content of greater than 93%. In some embodiments, the diffusion hardened zone has a hardness profile which is defined by a function selected from the group consisting of an error function, an exponential function, a near uniform distribution function, and any sequential combination thereof. In some embodiments, the first layer has a thickness which is greater than or equal to the thickness of said second layer and of any subsequent layers if present. In some embodiments, the diffusion hardened zone has a thickness of 5 to 70 microns. The diffusion hardened zone may have a thickness of 10 to 50 microns. The diffusion hardened zone may have a thickness of 15 to 30 microns. In some embodiments, the hardness of the diffusion hardened zone is at least 10% greater than that of the substrate In some embodiments, the medical implant is selected from the group consisting of a hip implant, a knee implant, and a spinal implant. In some embodiments, the substrate comprises an alloy of zirconium and niobium and has a niobium content of at least 1% (w/w). The substrate may comprise an alloy of zirconium and niobium has a niobium content of at least 10% (w/w). In some embodiments, the medical implant further comprises an oxygen-containing zirconium alloy overlaying said ceramic oxide or nitride on the surface of said implant, said alloy being in the metallic state.

In another aspect of the present invention there is a medical implant comprising: a substrate comprising zirconium or zirconium alloy; a diffusion hardened zone in contact with said substrate, said diffusion hardened zone comprising zirconium or zirconium alloy and a diffusion hardening species, said diffusion hardened zone having a thickness of greater than 5 microns; and, wherein the diffusion hardened zone has a layered structure comprising at least two distinct layers under metallographic analysis, said layered structure characterized by: a first layer on a surface of the implant; a second layer directly below said first layer, wherein said first layer is predominantly alpha phase zirconium; and, said layered structure having a concentration of diffusion hardening species which decreases in the direction of the substrate, said decrease of concentration of diffusion hardening species being defined by a function selected from the group consisting of an error function, an exponential function, a near uniform distribution function, and any sequential combination thereof. In some embodiments, the substrate further comprises titanium, tantalum, hafnium, niobium, and any combination thereof. In some embodiments, the diffusion hardening species is selected from the group consisting of oxygen, nitrogen, boron, carbon, and any combination thereof. Preferably, the diffusion hardening species comprises oxygen. In some embodiments, the diffusion hardened zone has a concentration of oxygen which decreases in the direction of the substrate, said decrease of oxygen concentration being defined by a function selected from the group consisting of an error function, an exponential function, a near uniform distribution function, and any sequential combination thereof. In some embodiments, the diffusion hardened zone has a hardness profile which is defined by a function selected from the group consisting of an error function, an exponential function, a near uniform distribution function any sequential combination thereof. In some embodiments, the first layer has a thickness which is greater than the thickness of said second layer and of any subsequent layers if present. In some embodiments, the diffusion hardened zone has a thickness of 5 to 70 microns. The diffusion hardened zone may have a thickness of 10 to 50 microns. The diffusion hardened zone may have a thickness of 15 to 30 microns. In some embodiments, the hardness of the diffusion hardened zone is at least 10% greater than that of the substrate. In some embodiments, the medical implant is selected from the group consisting of a hip implant, a knee implant, and a spinal implant. In some embodiments, the substrate comprises an alloy of zirconium and niobium has a niobium content of at least 1% (w/w). The substrate may comprise an alloy of zirconium, titanium and niobium and has a niobium content of at least 10% (w/w).

In another aspect of the present invention there is a method of making a surface hardened medical implant comprising the steps of: forming said medical implant of zirconium or zirconium alloy; and, further treating said implant by any one of (a), (b), or (c), wherein (a), (b), and (c) are defined as follows: (a) treating said implant in the presence of ceramic-forming species at a temperature of less than 700° C. for greater than 5 minutes; and, thereafter treating said implant under vacuum or inert gas at a temperature of from 500° C. to 1000° C. for greater than 1 hour; (b) treating said implant in the presence of ceramic-forming species at a temperature of from 500° C. to 1000° C.; and, thereafter treating said implant under vacuum or inert gas at a temperature less than 700° C.; (c) treating said implant in the presence of ceramic-forming species at a temperature of less than 700° C.; and, thereafter treating said implant under vacuum or inert gas at a temperature less than 700° C. In some embodiments, the method further comprises the step of treating said implant in the presence of a ceramic-forming species at a temperature less than 700° C. for greater than 5 minutes after said step of thereafter treating said implant under vacuum or inert gas. In some embodiments, the step of thereafter treating said implant under vacuum or inert gas is performed at a temperature of 600° C. to 700° C. In some embodiments, the step of treating said implant in the presence of ceramic-forming species is performed for between 5 minutes to 12 hours. In some embodiments, the step of thereafter treating said implant under vacuum or inert gas is performed for between 15 minutes to 30 hours. In some embodiments, the step of forming a medical implant of zirconium or zirconium alloy comprises forming said medical implant of zirconium alloy having an alloying element selected from the group consisting of titanium, tantalum, hafnium, niobium, and any combination thereof. In some embodiments, the step of forming comprises forming said medical implant of an alloy of zirconium and niobium, said alloy having a niobium content of at least 1% (w/w). In some embodiments, the step of forming comprises forming said medical implant of an alloy of zirconium and niobium, said alloy having a niobium content of at least 10% (w/w). In some embodiments, the step of treating said implant in the presence of ceramic-forming species and said step of thereafter treating said implant under vacuum or inert gas comprise treating said implant with a diffusion hardening species selected from the group consisting of oxygen, nitrogen, boron, carbon, and any combination thereof.

In another aspect of the present invention there is a method of making surface hardened medical implant comprising steps of: forming said medical implant of zirconium or zirconium alloy; forming an oxide, carbide, nitride, boride or combination thereof, on a surface of said implant at a temperature of from 500° C. to 1000° C. for greater than 2 hours; removing the formed oxide, carbide, nitride, boride, or combination thereof; and, thereafter re-forming an oxide, carbide, nitride, boride, or combination thereof, on a surface of said implant at a temperature of from 500° C. to 1000° C. for greater than 5 minutes.

In another aspect of the present invention there is a method of making surface hardened medical implant comprising steps of: forming said medical implant of zirconium or zirconium alloy; diffusing oxygen or nitrogen into said implant at a partial pressure of oxygen or nitrogen of less than 0.05 bar and at a temperature ranging from 500° C. to 1000° C. for greater than 2 hours; and, thereafter oxidizing or nitriding the implant between 500° C. to 1000° C. for greater than 10 minutes.

In another aspect of the present invention there is a method of making a surface hardened medical implant comprising the steps of: forming said medical implant of zirconium or zirconium alloy; oxidizing or nitriding said implant at a temperature of from 500° C. to 700° C. to form at least a 2 micron thick oxide or nitride; and, thereafter treating said implant under vacuum or inert gas at a temperature less than 700° C. to retain at least 0.1 microns oxide, to form at least 0.005 microns metallic hardened layer, and to form a diffusion zone having a thickness of at least 2 microns. In some embodiments, the substrate further comprises titanium, tantalum, niobium, hafnium, and any combination thereof. In some embodiments, the oxide or nitride thickness before said step of thereafter treating said implant under vacuum or inert gas is from 2 to 15 microns. In some embodiments, the oxide or nitride thickness after said step of thereafter treating said implant under vacuum or inert gas is from 0.1 to 10 microns. In some embodiments, the diffusion hardened zone is from 2 to 50 microns.

In another aspect of the present invention there is a medical implant produced by the process comprising the steps of: forming said medical implant of zirconium or zirconium alloy; further treating said implant by any one of (a), (b), or (c), wherein (a), (b), and (c) are defined as follows: (a) treating said implant in the presence of ceramic-forming species at a temperature of less than 700° C. for greater than 5 minutes; and, thereafter treating said implant under vacuum or inert gas at a temperature of from 500° C. to 1000° C. for greater than 1 hour; (b) treating said implant in the presence of ceramic-forming species at a temperature of from 500° C. to 1000° C.; and, thereafter treating said implant under vacuum or inert gas at a temperature less than 700° C.; (c) treating said implant in the presence of ceramic-forming species at a temperature of less than 700° C.; and, thereafter treating said implant under vacuum or inert gas at a temperature less than 700° C.

In another aspect of the present invention there is a medical implant, comprising: (a) a first implant portion comprising zirconium or zirconium alloy, said first implant portion having a bearing surface; (b) a second implant portion comprising zirconium or zirconium alloy, said second implant portion having bearing surface; (c) wherein the bearing surface of said first implant portion and the bearing surface of said second implant portion each have a size and shape to engage or cooperate with one another; (d) a diffusion hardened zone in contact with at least a portion of said zirconium or zirconium alloy, said diffusion hardened zone forming at least a part of the bearing surface of both of said first and second implant portions, said diffusion hardened zone comprising zirconium or zirconium alloy and a diffusion hardening species, said diffusion hardened zone having a thickness of greater than 2 microns; and, (e) a substantially defect-free ceramic layer in contact with said diffusion hardened zone and comprising a surface of said medical implant, said ceramic layer ranging in thickness from 0.1 to 25 microns; wherein the total thickness of the ceramic layer and the diffusion hardened zone is 5 microns or greater. In some embodiments, the ceramic layer comprises a secondary phase; and, the diffusion hardened zone has a layered structure comprising at least two distinct layers under metallographic analysis, the layered structure characterized by: a first layer directly below the ceramic layer, wherein the first layer is predominantly alpha phase zirconium; an interface between the first layer and the ceramic layer; and; a second layer directly below the first layer. In some embodiments, the substrate further comprises titanium, tantalum, hafnium, niobium, and any combination thereof. In some embodiments, the diffusion hardening species is selected from the group consisting of oxygen, nitrogen, boron, carbon, and any combination thereof. Preferably, the diffusion hardening species comprises oxygen. In some embodiments, the diffusion hardened zone has a concentration of oxygen which decreases in the direction of the substrate, said decrease of oxygen concentration being defined by a function selected from the group consisting of an error function, an exponential function, a near uniform distribution function, and any sequential combination thereof. In some embodiments, the ceramic oxide has monoclinic content of greater than 93%. In some embodiments, the diffusion hardened zone has a hardness profile which is defined by a function selected from the group consisting of an error function, an exponential function, a near uniform distribution function and any sequential combination thereof. In some embodiments, the first layer has a thickness which is greater than or equal to the thickness of said second layer and of any subsequent layers if present. In some embodiments, the diffusion hardened zone has a thickness of 5 to 70 microns. Tithe diffusion hardened zone may have a thickness of 10 to 50 microns. The diffusion hardened zone may have a thickness of 15 to 30 microns. In some embodiments, the hardness of the diffusion hardened zone is at least 10% greater than that of the substrate. In some embodiments, the medical implant is selected from the group consisting of a hip implant, a knee implant, and a spinal implant. In some embodiments, the substrate comprises an alloy of zirconium and niobium and has a niobium content of at least 1% (w/w). In some embodiments, the substrate comprises an alloy of zirconium and niobium has a niobium content of at least 10% (w/w). In some embodiments, the medical implant further comprises an oxygen-containing zirconium alloy overlaying said ceramic oxide or nitride on the surface of said implant, said alloy being in the metallic state.

In another aspect of the present invention, there is medical implant, comprising: (a) a first implant portion comprising zirconium or zirconium alloy, said first implant portion having a bearing surface; (b) a second implant portion comprising zirconium or zirconium alloy, said second implant portion having bearing surface; (c) wherein the bearing surface of said first implant portion and the bearing surface of said second implant portion each have a size and shape to engage or cooperate with one another; (d) a diffusion hardened zone in contact with at least a portion of said zirconium or zirconium alloy, said diffusion hardened zone forming at least a part of the bearing surface of both of said first and second implant portions, said diffusion hardened zone comprising zirconium or zirconium alloy and a diffusion hardening species, said diffusion hardened zone having a thickness of greater than 5 microns; wherein the diffusion hardened zone has a layered structure comprising at least two distinct layers under metallographic analysis, said layered structure characterized by: a first layer on a surface of the implant; a second layer directly below said first layer, wherein said first layer is predominantly alpha phase zirconium; and, said diffusion hardened zone having a concentration of diffusion hardening species which decreases in the direction of the substrate, said decrease of concentration of diffusion hardening species being defined by a function selected from the group consisting of an error function, an exponential function, a near uniform distribution function, and any sequential combination thereof. In some embodiments, the substrate further comprises titanium, tantalum, hafnium, niobium, and any combination thereof. In some embodiments, the diffusion hardening species is selected from the group consisting of oxygen, nitrogen, boron, carbon, and any combination thereof. Preferably, the diffusion hardening species comprises oxygen. In some embodiments, the diffusion hardened zone has a concentration of oxygen which decreases in the direction of the substrate, said decrease of oxygen concentration being defined by a function selected from the group consisting of an error function, an exponential function, a near uniform distribution function, and any sequential combination thereof. In some embodiments, the diffusion hardened zone has a hardness profile which is defined by a function selected from the group consisting of an error function, an exponential function, a near uniform distribution function and any sequential combination thereof. In some embodiments, the first layer has a thickness which is greater than the thickness of said second layer and of any subsequent layers if present. In some embodiments, the diffusion hardened zone has a thickness of 5 to 70 microns. The diffusion hardened zone may have a thickness of 10 to 50 microns. The diffusion hardened zone may have a thickness of 15 to 30 microns In some embodiments, the hardness of the diffusion hardened zone is at least 10% greater than that of the substrate. In some embodiments, the medical implant is selected from the group consisting of a hip implant, a knee implant, and a spinal implant. In some embodiments, the substrate comprises an alloy of zirconium and niobium has a niobium content of at least 1% (w/w). In some embodiments, the substrate comprises an alloy of zirconium, titanium and niobium and has a niobium content of at least 10% (w/w).

In another aspect of the present invention, there is a medical implant comprising: (a) a first implant portion, said first implant portion having a bearing surface; (b) a second implant portion, said second implant portion having a bearing surface; (c) wherein the bearing surface of said first implant portion and the bearing surface of said second implant portion each have a size and shape to engage or cooperate with one another; (d) wherein one or both of the two portions of the medical implant comprises a biocompatible alloy having an elastic modulus less than 200 GPa; and, (e) wherein the difference in radius of the mating portions is greater than about 50 microns. In some embodiments, one or both of said first implant portion and said second implant portion further comprises: a substrate; a diffusion hardened zone in contact with said substrate, said diffusion hardened zone comprising a diffusion hardening species, said diffusion hardened zone having a thickness of greater than 2 microns; and, a substantially defect-free ceramic layer in contact with said diffusion hardened zone and comprising a surface of said medical implant, said ceramic layer ranging in thickness from 0.1 to 25 microns; and, wherein the total thickness of the ceramic layer and the diffusion hardened zone is 5 microns or greater. In some embodiments, one or both of said first implant portion and said second implant portion further comprises: the ceramic layer comprises a secondary phase; and, the diffusion hardened zone has a layered structure comprising at least two distinct layers under metallographic analysis, the layered structure characterized by: a first layer directly below the ceramic layer; an interface between the first layer and the ceramic layer; and; a second layer directly below the first layer. In some embodiments, one or both of said first implant portion and said second implant portion further comprises: a substrate; a diffusion hardened zone in contact with said substrate, said diffusion hardened zone comprising a diffusion hardening species, said diffusion hardened zone having a thickness of greater than 5 microns; and, wherein the diffusion hardened zone has a layered structure comprising at least two distinct layers under metallographic analysis, said layered structure characterized by: a first layer on a surface of the implant; a second layer directly below said first layer; and, said diffusion hardened zone having a concentration of diffusion hardening species which decreases in the direction of the substrate, said decrease of concentration of diffusion hardening species being defined by a function selected from the group consisting of an error function, an exponential function, a near uniform distribution function, and any sequential combination thereof. In some embodiments, one or both of said first implant portion and said second implant portion further comprises: a substrate; a diffusion hardened zone in contact with said substrate, said diffusion hardened zone comprising a diffusion hardening species, said diffusion hardened zone having a thickness of greater than 2 microns; and, a substantially defect-free ceramic layer in contact with said diffusion hardened zone and comprising a surface of said medical implant, said ceramic layer ranging in thickness from 0.1 to 25 microns; and, wherein the total thickness of the ceramic layer and the diffusion hardened zone is 5 microns or greater. In some embodiments, one or both of said first implant portion and said second implant portion further comprises: the ceramic layer comprises a secondary phase; and, the diffusion hardened zone has a layered structure comprising at least two distinct layers under metallographic analysis, the layered structure characterized by: a first layer directly below the ceramic layer; an interface between the first layer and the ceramic layer; and; a second layer directly below the first layer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
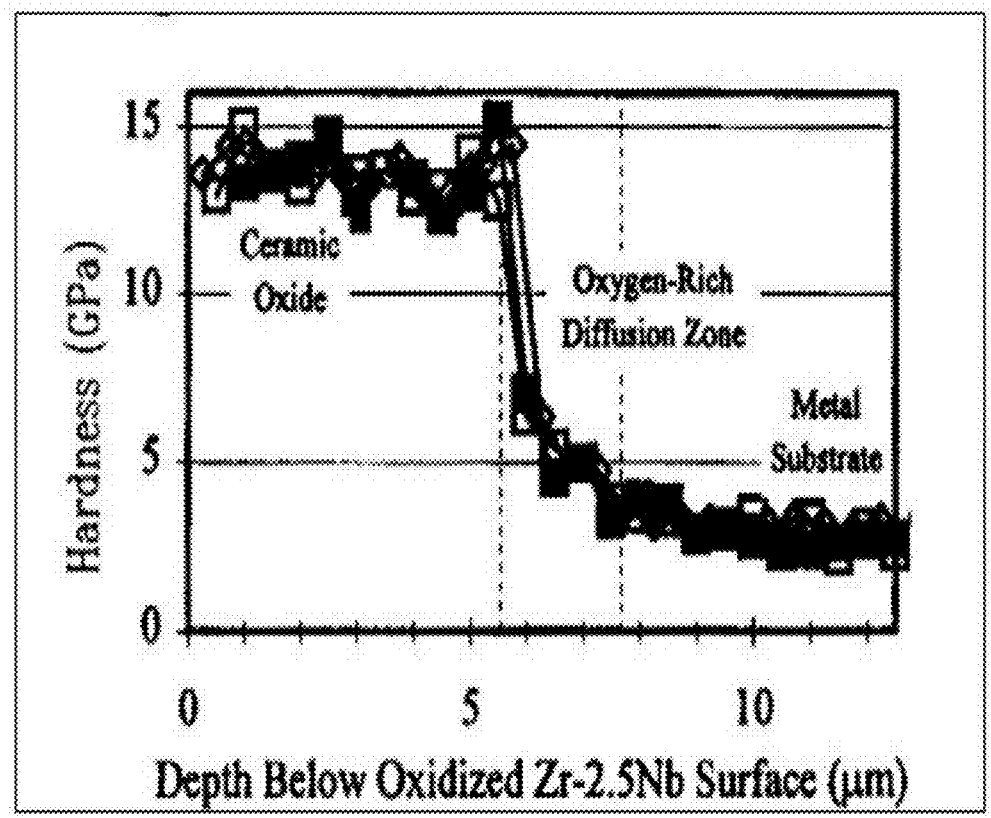
FIG. 1 shows the hardness profile of Davidson-type oxidized zirconium composition. The thickness of the diffusion zone is 1.5 to 2 microns (Long et. al.)

As used herein, "a" or "an" means one or more. Unless otherwise indicated, the singular contains the plural and the plural contains the singular.

As used herein, "zirconium alloy" is defined broadly, and includes alloys having at least 5% (w/w) zirconium. The alloys can be of zirconium, titanium, hafnium and niobium. The alloys can be polycrystalline or amorphous or single crystals or combinations of same.

As used herein, "ceramic" is defined as a chemical compound of a metal (or a metal constituent in an alloy) and one or more non-metals, including carbon, oxygen, nitrogen, boron, and combinations thereof. While the preferred embodiment of the ceramic of the present invention is an oxide, the ceramic of the present invention includes oxides, carbides, nitrides, borides, and any combination thereof. As used herein, "ceramic layer" is defined as a stratum of material consisting of ceramic which forms a part of a greater material. As used herein, the term "ceramic coating" refers to a surface transformed layer, surface film, surface oxide, nitride, carbide, boride (or combination thereof) present on the alloy or metal substrate.

As used herein, "ceramic-forming species" is defined as oxygen, carbon, nitrogen, boron, and any combination thereof. It is preferable that the ceramic-forming species be in the gas phase during the formation of the ceramic layer, although it is possible and within the scope of the present invention wherein the ceramic-forming species is present in a phase other than the gas phase. One non-limiting example of a non-gas phase embodiment is wherein the ceramic-forming species is in the solid phase in contact with the substrate to which it is to be introduced. The ceramic-forming species, in addition to forming a ceramic, also acts as a diffusion hardening species in the formation of a diffusion zone.

The "diffusion zone" is defined as the zone below the ceramic surface (if a ceramic surface is present) or at the surface itself (if a ceramic surface is not present) and that comprises a diffusion hardening species. "Diffusion hardening species" is defined as carbon, oxygen, nitrogen, boron, or any combination thereof. The "diffusion hardened zone" is defined as that portion of the diffusion zone having hardness at least 1.1 times greater than the substrate hardness.

As used herein, "biocompatible alloy" is defined as the alloy combinations that are currently used in orthopedic industry. Examples of such alloys include cobalt-chromium-molybdenum, titanium-aluminum-vanadium, nickel-titanium and zirconium-niobium. The other biocompatible alloys that are referred in this invention are the alloys that are made from either zirconium or titanium or tantalum or niobium or hafnium or combination thereof.

As used herein, the term "vacuum" refers to a pressure of less than about $10^{-2}$ torr.

Implants comprising Davidson-type oxidized zirconium have been shown to reduce polyethylene wear significantly. This significant reduction in wear is attributed to its ceramic surface. The oxidized zirconium implant typically has 4 to 5 micron thick ceramic surface (zirconium oxide) that is formed by a thermally driven diffusion process in air. Beneath the zirconium oxide is a hard, oxygen-rich diffusion layer of approximately 1.5 to 2 microns. The totality of hardened zones (oxide plus diffusion hardened alloy) render the implant resistant to microscopic abrasion (third bodies such as bone cement, bone chips, metal debris, etc.) and slightly less resistant to macroscopic impact (surgical instrumentation and from dislocation/subluxation contact with metallic acetabular shells). However, like all conventional medical implant materials, Davidson-type oxidized zirconium implants are susceptible to damage caused by dislocation and subluxation (macroscopic). Although not intending to be bound by theory, it is believed that this susceptibility is due to the relatively small thickness of the total hardened zones (5 micron oxide plus 1.5 to 2 micron diffusion zone) in the Davidson-type oxidized zirconium products. Although Davidson-type oxidized zirconium implants perform better than most materials in hard-on-soft applications, the small hardened zone is not ideal for hard-on-hard bearing applications. The abrasion resistance of oxidized zirconium and other common implant alloys can be improved by increasing the depth of totality of the hardened zones. Such hardened alloys are suitable for articulation against soft polymers (such as UHMWPE, XLPE, polyurethane, etc) and in hard-on-hard bearing applications against like hardened alloys, against CoCr alloys, ceramics (alumina, silicon nitride, silicon carbide, zirconia, etc), and other hard materials such as diamond, diamond-like carbon, etc.

Figure 6:
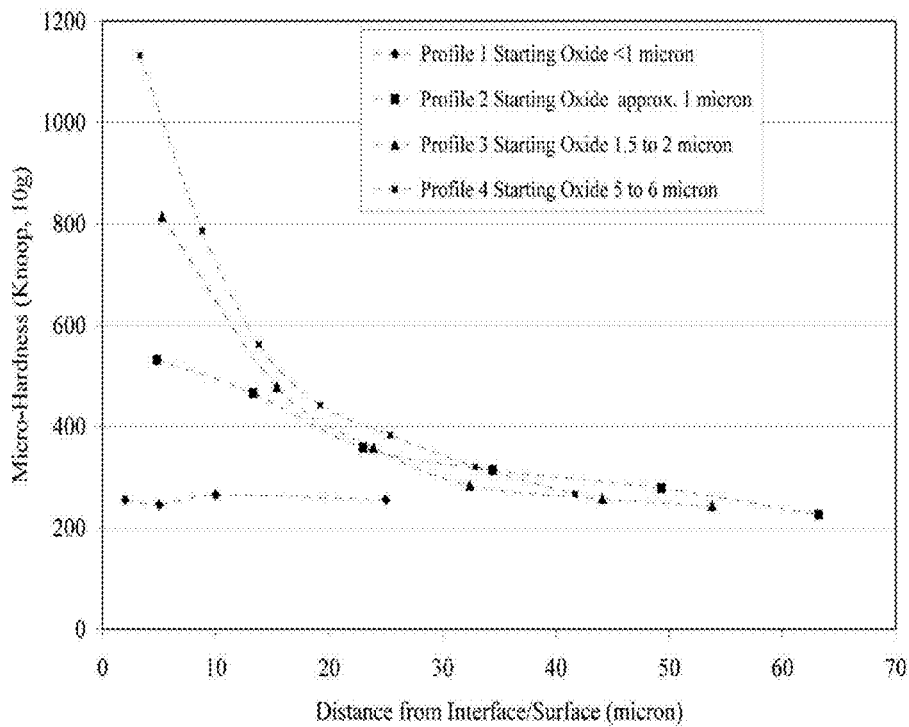
FIG. 6 shows hardness profiles obtained on Zr-2.5Nb samples after vacuum diffusion process (685° C. for 10 hours). The starting oxide represents oxide thickness prior to vacuum diffusion treatment. The oxidation was carried out at 635° C. for different times to produce different starting oxide thickness.
Figure 7:
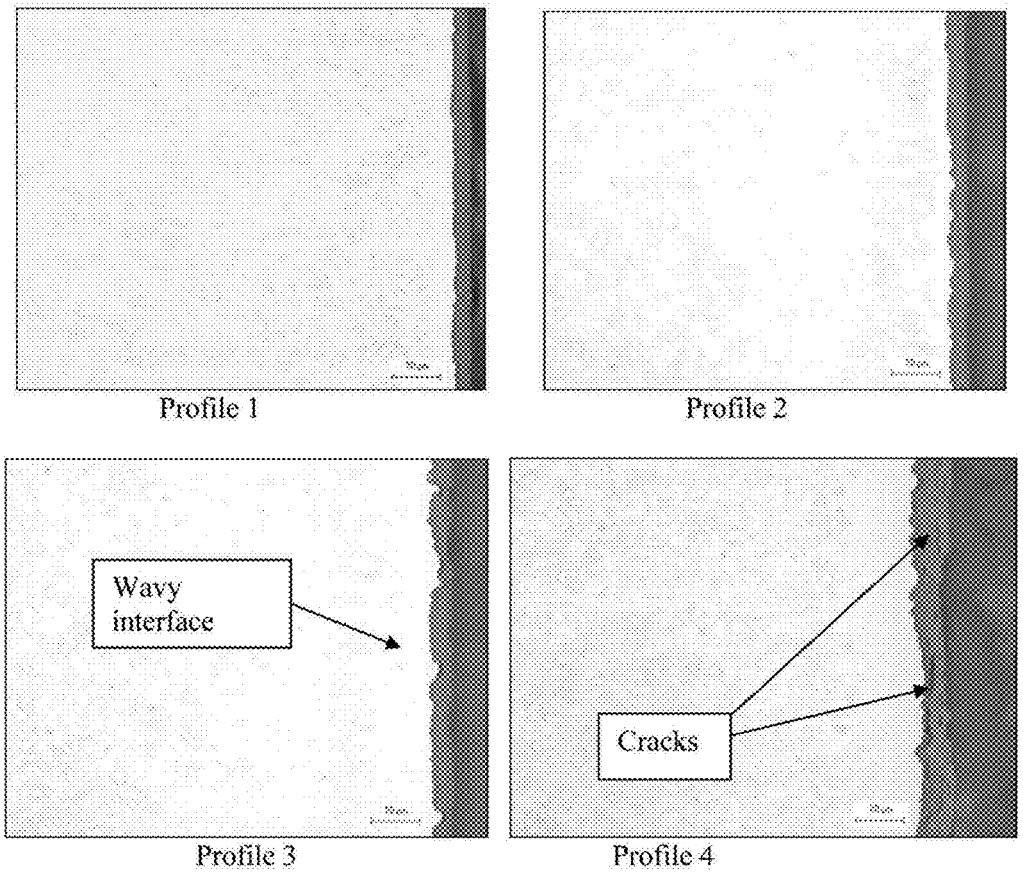
FIG. 7 shows metallographic images of samples with hardness profile obtained in FIG. 3 were re-oxidized at 635° C. for 60 minutes.

FIG. 6 shows four types of hardness profiles obtained on Zr-2.5Nb alloy samples using an embodiment of the method of the present invention. The four profiles obtained are Profile 1: uniform function, Profile 2: a combination of uniform function and exponential function, Profile 3: a combination of exponential function and error function, Profile 4: error function. As will be discussed in detail, the resultant shape of the hardness profile was carefully controlled by the oxide thickness, oxidation and vacuum treatment temperatures and time. In this particular example, the starting oxide thickness was varied by varying oxidation time at a constant temperature of 635° C. Samples were oxidized for 5 minutes, 15 minutes, 30 minutes and 60 minutes respectively. All the samples were vacuum treated at 685° C. for 10 hours. After vacuum treatment the four samples produced four different profiles as shown in FIG. 6. The oxide was retained on sample with profile 4 and was completely dissolved on samples with profiles 1 to 3. Each of these profiles can have a distinct advantage over the other. For example, if the oxidation step needs to be repeated after vacuum treatment to form oxide, then Profiles 1 to 3 may produce a high integrity predominantly defect-free oxide compared to Profile 4. FIG. 7 shows metallographic images of the oxide formed on samples with different profiles. These samples were oxidized after the vacuum treatment at 635° C. for 1 hour to produce 5 to 6 micron thick oxide. As can be seen, oxide on the Profile 4 is cracked and non-uniform compared to that formed in Profiles 1 to 3. This is believed to be caused by lack of plasticity of the diffusion hardened zone that cannot accommodate stresses generated during re-oxidation. This example illustrates another embodiment of the invention that will be disclosed. If re-oxidation of the alloy samples is desired after diffusion hardening process, it is important to obtain an adequate diffusion profile (Profiles 1 to 3). The appropriate diffusion profile ensures a substantially defect-free oxide formation after the vacuum treatment. The oxidation process is typically accompanied by the volume expansion of the surface (oxide). If the stresses generated during volume expansion are not accommodated in the substrate, it can lead to defects such as cracks and pores in the oxide. An example of such defects in the oxide is shown in FIG. 7 (Profile 4). Cracks and pores can compromise integrity of the oxide and may lead to spalling of the oxide. Another type of defect that is anticipated in this disclosure is the uniformity of the oxide-metal interface. FIG. 7 shows an example of wavy interface formed on samples of Profile 3. There are few pores and cracks but there are areas where the oxide thickness is less than 50% of the nominal oxide thickness. Such type of wavy interface may be unacceptable for a medical implant since there is a potential compromise of the integrity of the oxide.

Figure 2:
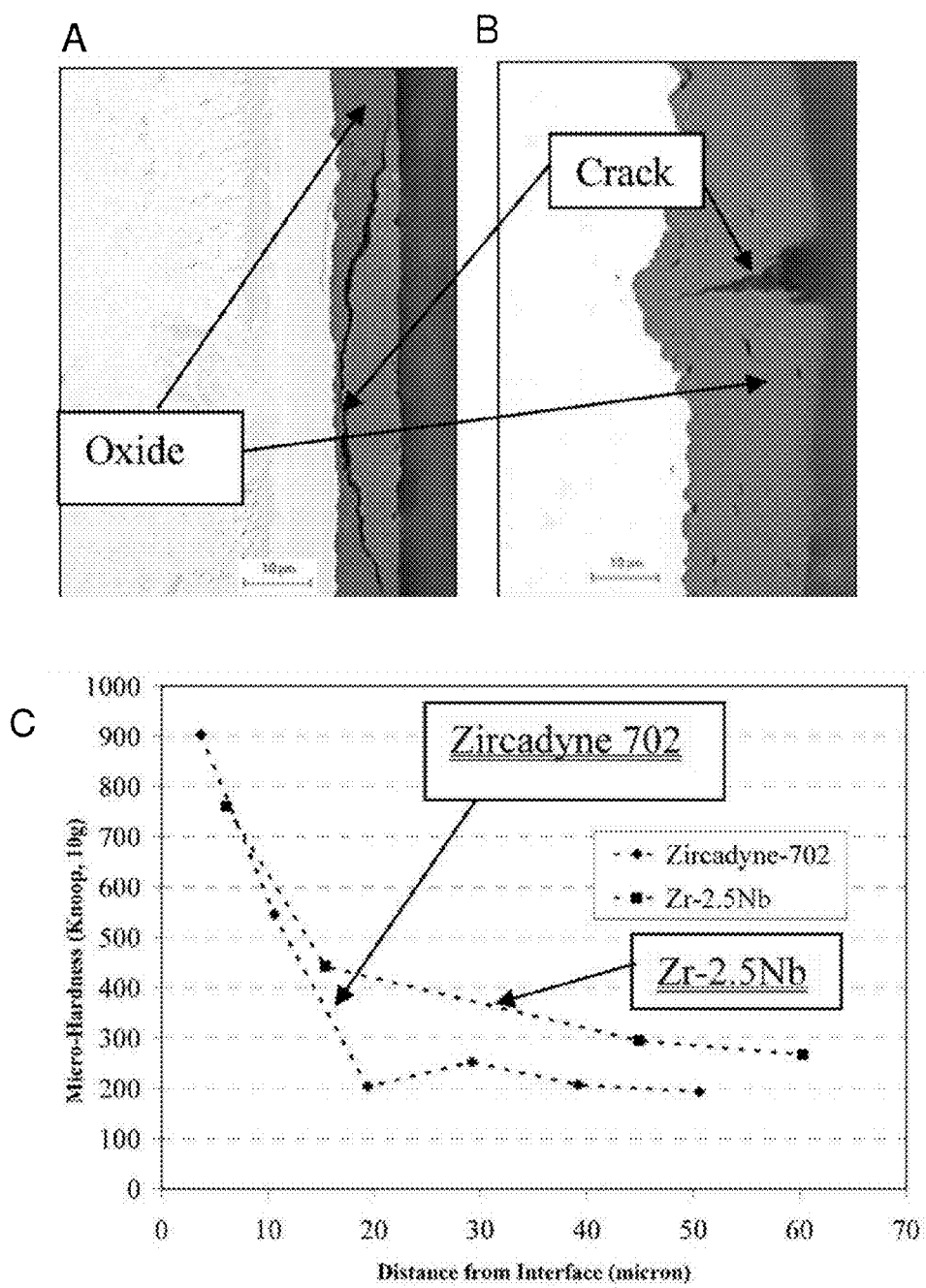
FIGS. 2 (a) and (b) are metallographic images of Zircadyne 702 and Zr-2.5Nb oxidized following the teachings of Kemp; (c) micro-hardness profile of the diffusion hardened zone FIGS. 3 (a) and (b) are metallographic images of Ti—Zr—Nb and Zr-2.5Nb oxidized by following teachings of Davidson; (c) Micro-hardness profile of diffusion hardened zone.
Figure 3:
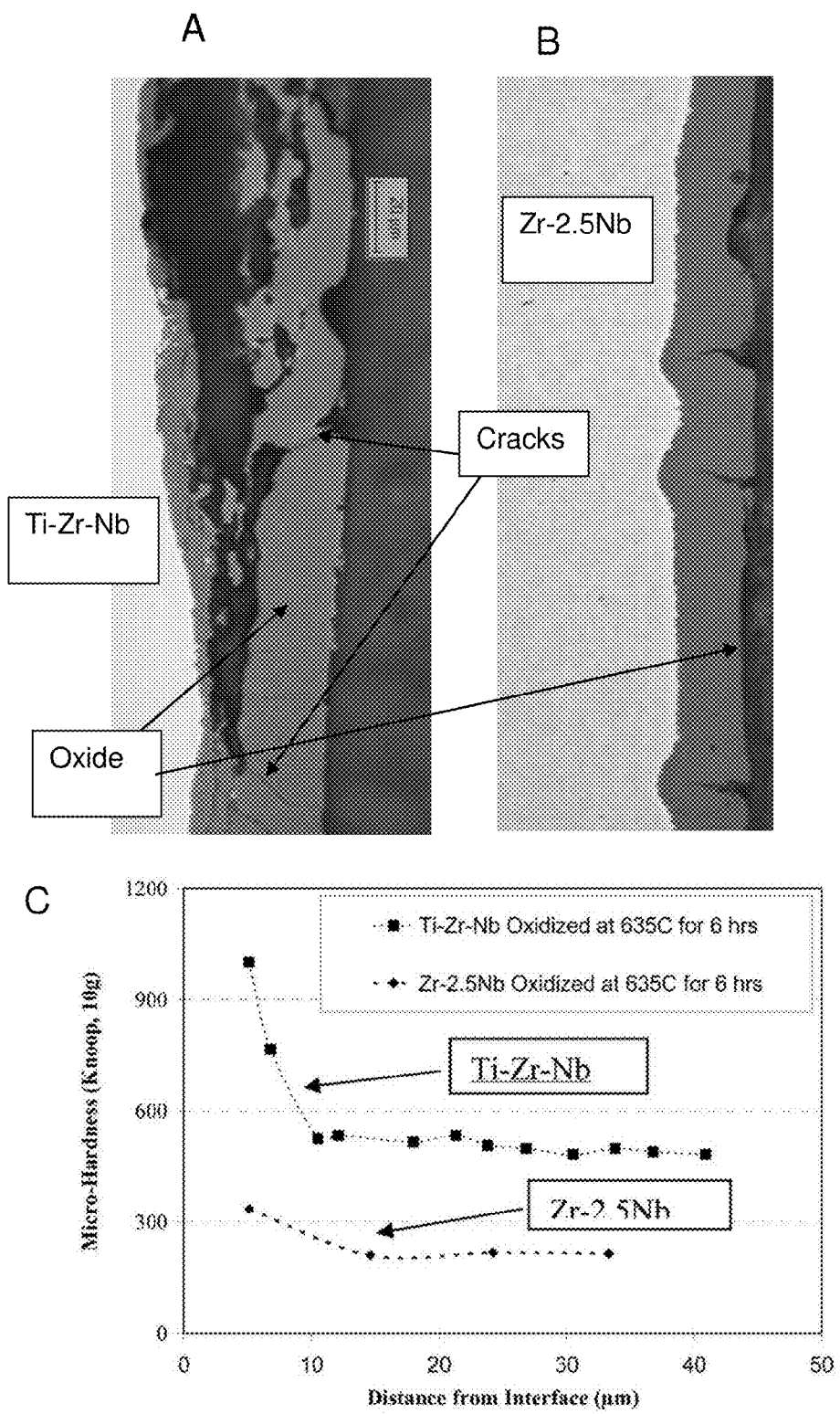
Figure 4:
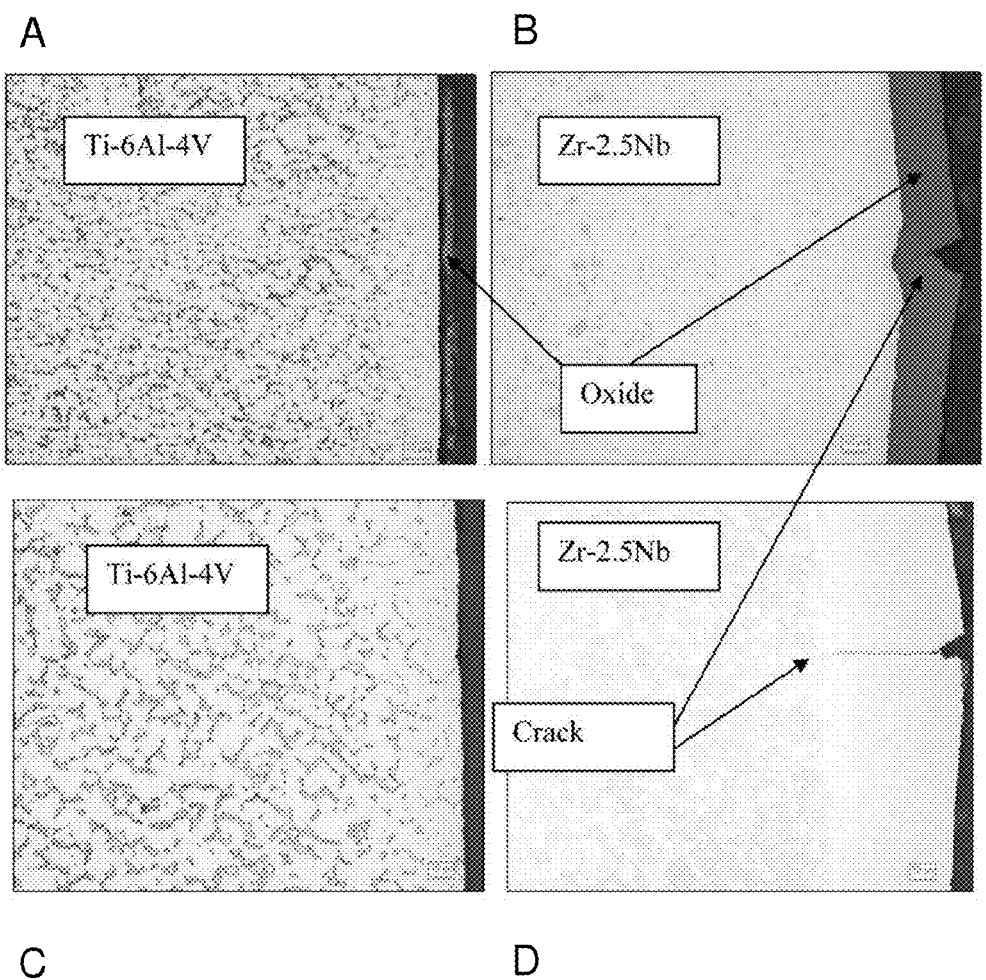
FIGS. 4 (a) and (b) show samples of Ti-6Al-4V and Zr-2.5Nb oxidized at 850° C. for 0.3 hours respectively; (c) and (d) show samples of Ti-6Al-4V and Zr-2.5Nb diffusion hardened at 850° C. for 22 hours respectively.
Figure 5:
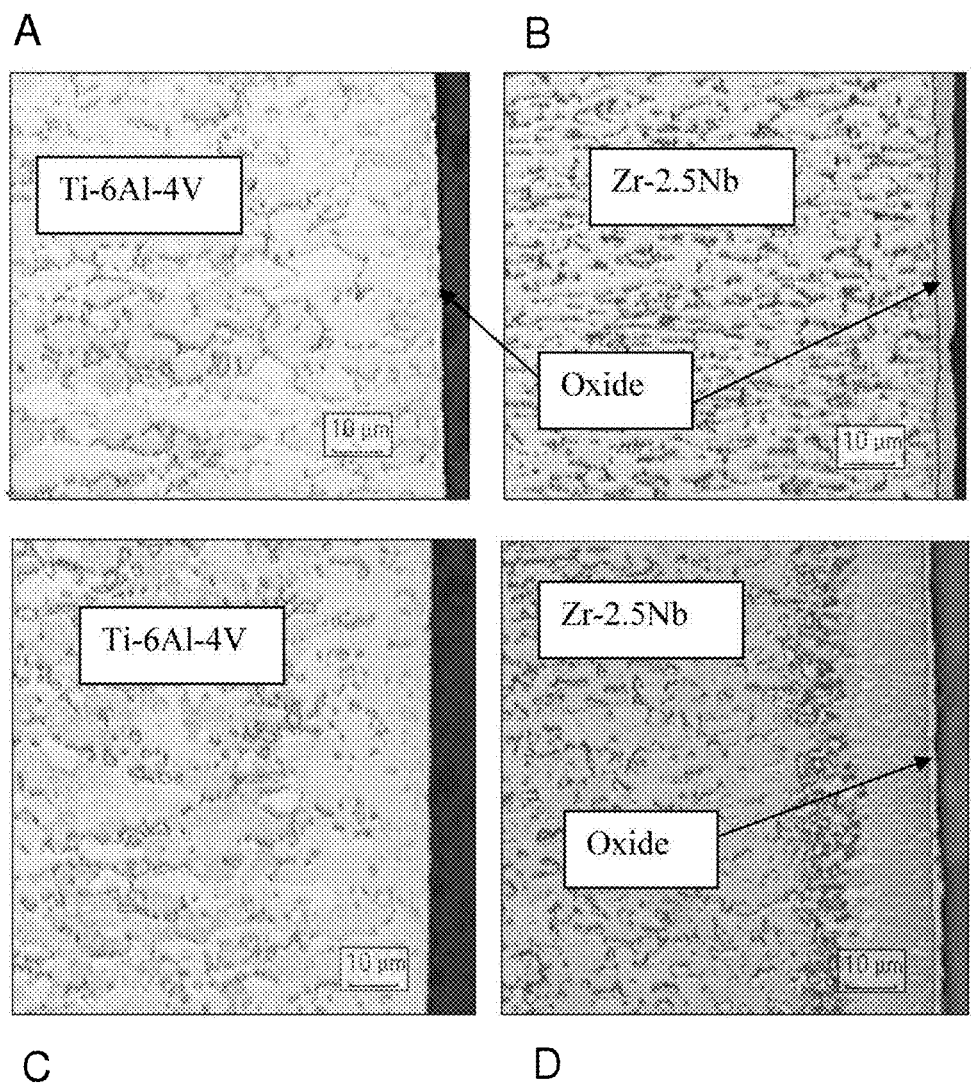
FIGS. 5 (a) and (b) show samples of Ti-6Al-4V and Zr-2.5Nb oxidized at 600° C. for 75 minutes respectively; (c) and (d) show samples of Ti-6Al-4V and Zr-2.5Nb diffusion hardened at 685° C. for 10 hours respectively, (e) shows the hardness profile of Ti-6Al-4V and Zr-2.5Nb after diffusion hardening.
Figure 5E:
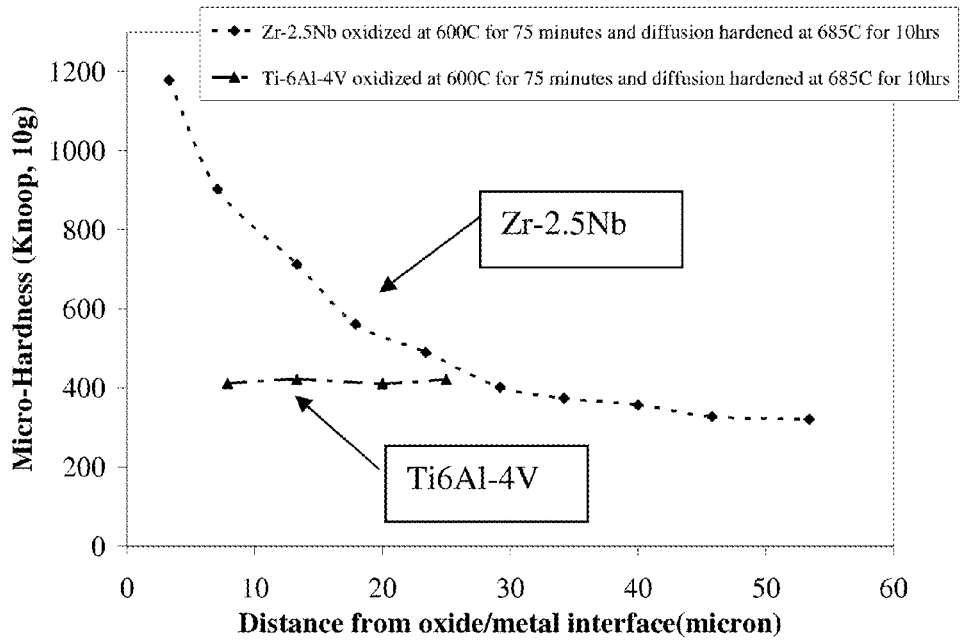

In a medical implant application, it is desirable that the oxide (or other ceramic layer) formed is substantially defect-free. When the oxide is formed on zirconium alloy substrate, there is expansion of volume as oxygen atoms are added in the zirconium matrix. This volume expansion leads to significant amount of stresses that need to be dissipated. If the substrate underneath is significantly brittle to start with, pores and cracks may form in the oxide to dissipate the stresses. It may also lead to a wavy interface between the oxide and metal. It sometimes may lead to spalling of the oxide as well. The defects in the oxide can be broadly classified as pores and cracks. The pores can be circular or elongated and may be on the surface or at the interface. The cracks can be perpendicular to the oxide metal interface, and/or may be parallel to the oxide metal interface. Another type of defect that is anticipated in this disclosure is the wavy oxide metal interface and delaminated or spalled oxide. One object of the present invention is to produce a substantially defect-free ceramic layer with a thicker diffusion hardened zone. As mentioned previously, following the prior art teachings of Kemp and Davidson, a thicker diffusion zone can be obtained but it produces an oxide that is not substantially defect-free. For example, FIG. 2(a) shows that the oxide is separated from the oxide metal interface. FIG. 2(b) shows a crack perpendicular to the oxide metal interface. FIG. 7 (profile 4) shows oxide with several elongated pores, and cracks that are parallel to the interface. FIG. 7 (profile 3) shows an example of another type of defect where the oxide metal interface is wavy. It is the object of this invention to form a ceramic layer that is substantially free of such defects. The defects in the ceramic layer are evaluated on a cross-sectional metallographic sample at 1000× magnification with field of view of approximately 100×80 microns. The substantially defect-free ceramic layer of the present invention is characterized by a) average pore diameter smaller than 15% of ceramic layer thickness, b) average crack length parallel to the ceramic layer/metal interface to be less than 25% of ceramic layer thickness, (c) average opening width of crack perpendicular to the ceramic layer/metal interface to be less than 15% of ceramic layer thickness and (d) the difference between average and minimum ceramic layer thickness to be less than 50% of the nominal oxide thickness. It is possible that the all defects described above may appear in one field of view or only few of them in one view and all remaining in another view. The defect-free ceramic layer of the present invention is defined as that in which above mentioned defects are not seen in at least 3 out of 5 fields of randomly chosen views. The ceramic layer which is substantially free of such defects is termed as defect-free.

In the present invention, there is medical implant and a method of producing the medical implant; the medical implant having a defect-free ceramic layer comprising a secondary phase along with diffusion hardened zone underneath the ceramic layer. This is accomplished by careful control of the ceramic formation and diffusion hardening temperatures. In one aspect of this invention, this leads to a preferred profile of the hardened zone beneath the ceramic layer. In another aspect of the invention, the ceramic layer is preferentially retained on the surface and is comprised of a secondary phase. In another aspect of invention, an adequate hardness profile is obtained if re-formation of the ceramic layer is required after diffusion hardening. In another aspect of the present invention, the diffusion zone is comprised of a layered structure. In another aspect of the present invention, a hardened metallic film is formed on the surface of the ceramic layer.

Figure 8:
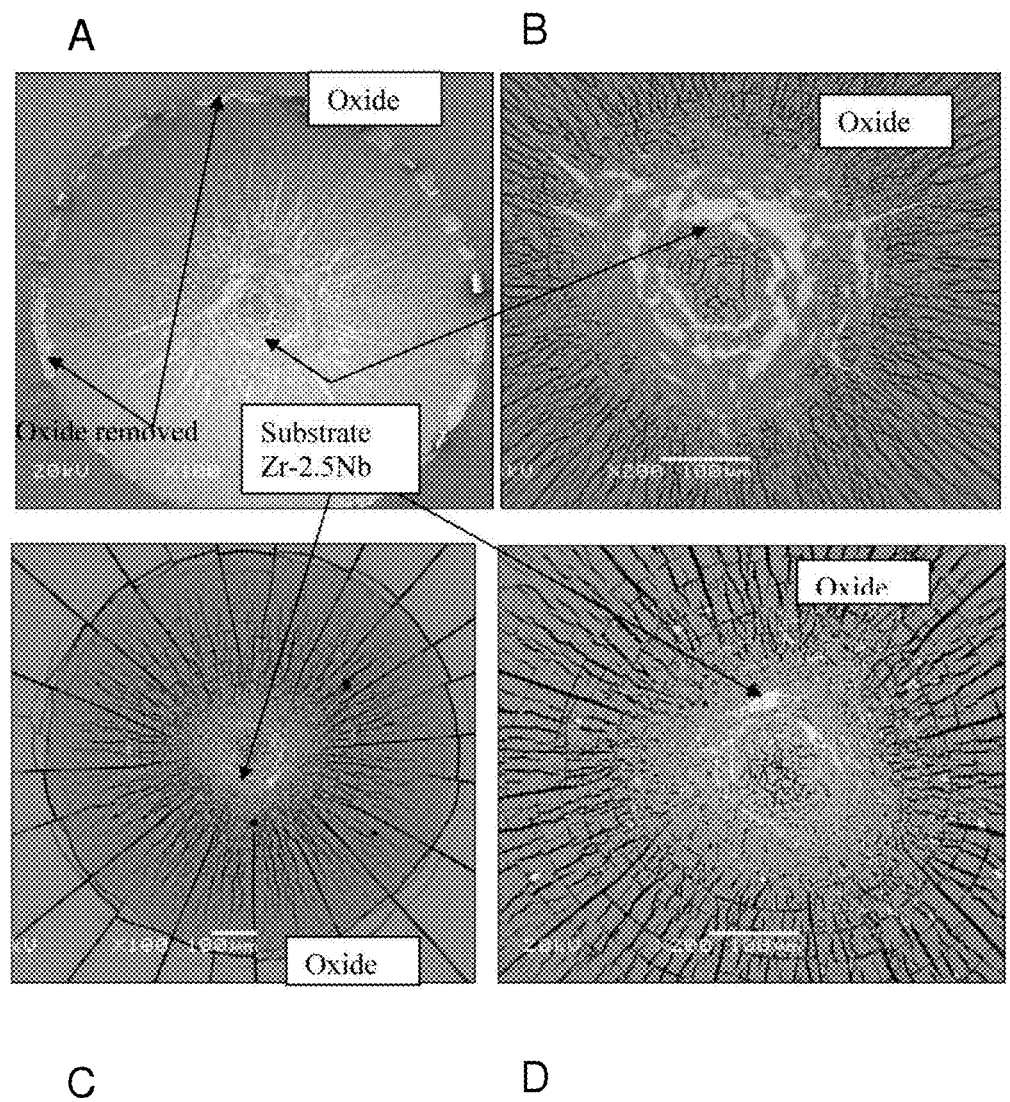
FIG. 8 illustrates Rockwell indents showing the damage resistance of (a) and (b) Davidson-type oxidized zirconium composition and (c) and (d) composition disclosed in this invention with a total hardening depth of 20 to 25 microns.
Figure 9:
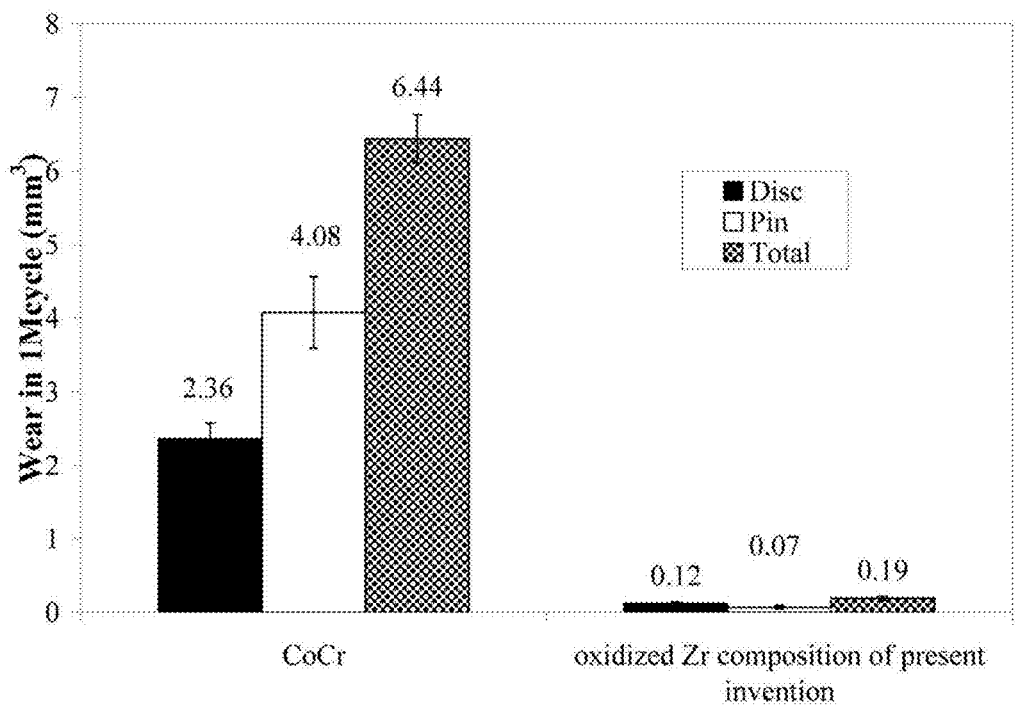
FIG. 9 shows wear results of pin-on-disk testing of high carbon cast CoCr against itself and one of the oxidized zirconium compositions against itself (total hardened zone 20 to 25 microns) disclosed in this invention.

The effect of the hardened zone on damage tolerance was evaluated by a Rockwell indent and by carrying out a wear test. FIG. 8 shows back scattered electron images of the indents on Davidson-type oxidized zirconium composition and that disclosed in this invention. The damage was produced on a flat disk by indenting the surface with a Rockwell indenter (diamond) with a load of 150 lbf. FIGS. 8 (a) and 8 (b) show damage produced on the Davidson-type oxidized zirconium composition. It should be noted that applied stress is much greater than that expected in the body. The indent has caused the oxide to crack in circumferential and in radial direction. The bright area in the center is exposed Zr-2.5Nb substrate. The grayish area is oxide. Due to the amount of strain induced during indentation, oxide at the edges of the indent is cracked and removed along with the substrate material. FIGS. 8 (c) and 8 (d) show damage produced on one of the compositions of the present invention. This sample was oxidized at 635° C. for 75 minutes and then diffusion hardened at 685° C. for 10 hours at a pressure of $10^{-4}$ torr. The oxide (approximately 4 micron thick) was retained on this sample. The hardened metallic layer formed on the surface was removed by diamond polishing before the test. The total hardened zone of this sample is 20 to 25 microns. The damage on this sample is significantly less for the new composition than it is for the Davidson-type oxidized zirconium composition. Less amount of substrate Zr-2.5Nb is exposed at the center. The ceramic layer is not removed along the edges of the sample. Although the Davidson-type oxidized zirconium composition was a great advance for medical implants and continues to be superior to other conventional medical materials, this example shows the marked improvement in the damage resistance obtained over the Davidson-type oxidized zirconium compositions. FIG. 9 shows results of a wear study when a composition of the present invention (in this case, a ceramic oxide) was articulated against itself in a pin on disk test. The test was run on a pin on disk tester at an applied load of 10 N for 1 Mcycle. Load was increased to 50N at approximately 0.5 Mcycles. Lactated ringer's solution was used as the test medium. The disks were flat and the pins had 100 mm radius. The disks and pins of Zr-2.5Nb were oxidized at 635° C. for 120 minutes and then diffusion hardened at 685° C. for 10 hours. The oxide (approximately 7 microns) was retained after diffusion hardening process. The metallic layer and part of the oxide was removed by diamond polishing before the test. The pins were used in as diffusion hardened condition and comprised of metallic hardened layer over the oxide and the layered diffusion zone underneath the oxide. A comparison was also made to the current standard of hard-on-hard bearings, high carbon cast CoCr. The wear of the new composition was approximately 34 times less than that of CoCr against CoCr couple. The pin-on disk test does not take into account the geometrical constraints encountered in a hip, knee or spinal joint. Another object of the present invention is to also account for the geometrical aspects of the joint. It is well-known that wear in a hard-on-hard hip joint is biphasic. The first phase of wear is a run-in wear and the second phase is steady-state wear. In the run-in phase, the asperities of the mating components wear out. After the running in wear, based on the component geometry and the stiffness of the components, a fluid film is formed between the mating components. This is typically termed as steady-state wear. The steady-state wear is typically less than run-in wear. One of the approaches to reduce the run-in and steady-state wear is to use metal-ceramic articulation as taught by Fisher et al (U.S. Patent Application 2005/0033442) and Khandkar et al (U.S. Pat. No. 6,881,229). Although this will reduce metal-ion release, the fracture risk of the ceramic component still prevails.

In another approach, Lippincott and Medley (U.S. Pat. No. 6,059,830) teach applying geometrical constraints to the mating hip components. The '830 patent teaches the use of components such that the radius difference of the mating components is less than 50 microns. This small difference in radius will promote thicker fluid film formation and thus reduced wear of mating metallic components. The disadvantage of this method is that a sophisticated manufacturing set-up is required to produce components with such tight tolerances. The inventors of the present invention have found that such a demanding manufacturing approach is not necessary. A thicker fluid film can also be formed by using lower elastic modulus (E) alloys such as, for example, Zr and/or Ti alloys (having, for example, E<120 GPa), instead of using higher elastic modulus alloys such as CoCr alloys (having, for example, E typically greater than 200 GPa). This allows for other metal and metal alloy systems (other than zirconium and/or titanium) to be used in the present invention as a substrate of the medical implant when the elastic modulus of such metal and metal alloy systems is less than 200 GPa. In one aspect of invention, the radial difference between the mating components of the present invention is kept above 50 microns and based on the radius of the component used can be as high as 150 microns or greater.

Figure 10:
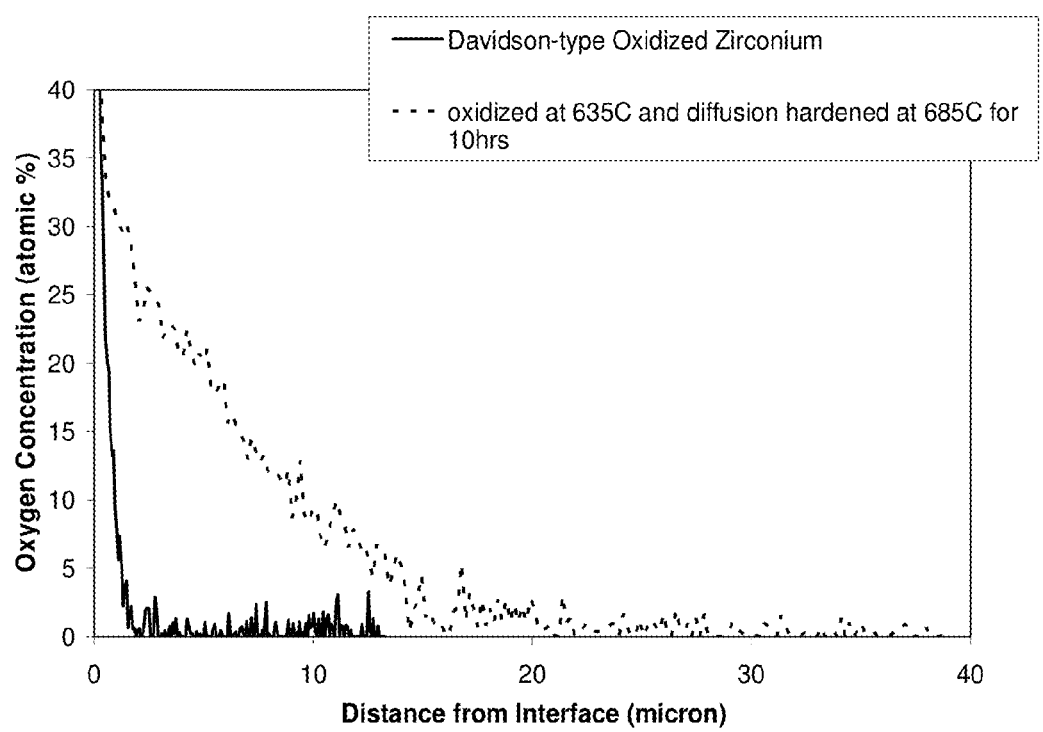
FIG. 10 shows the oxygen concentration profile of the diffusion zone. Analyses were carried out using a scanning auger microprobe with accelerating voltage of 10 kV; probe current of 18 nA and electron beam at 30° from sample normal. Oxide was retained on the sample after the vacuum treatment.
Figure 11:
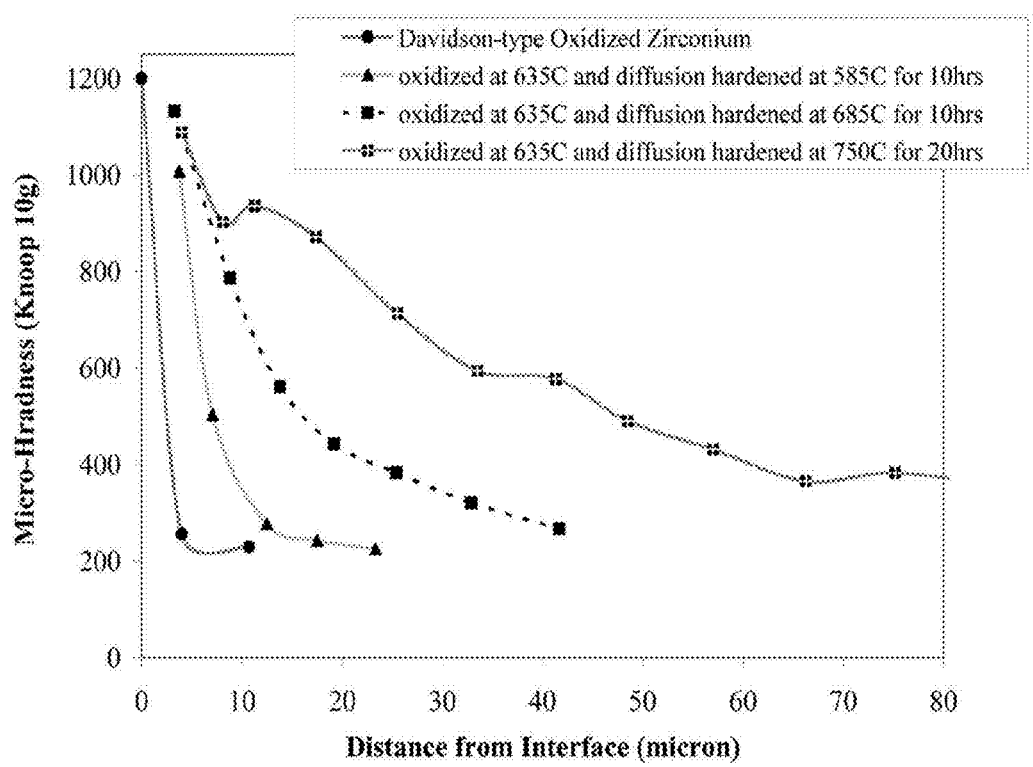
FIG. 11 illustrates the micro-hardness profile of Davidson-type oxidized zirconium composition and some of the compositions disclosed in this invention. Micro-hardness was carried out using a Knoop indenter at a load of 10 g.
Figure 12:
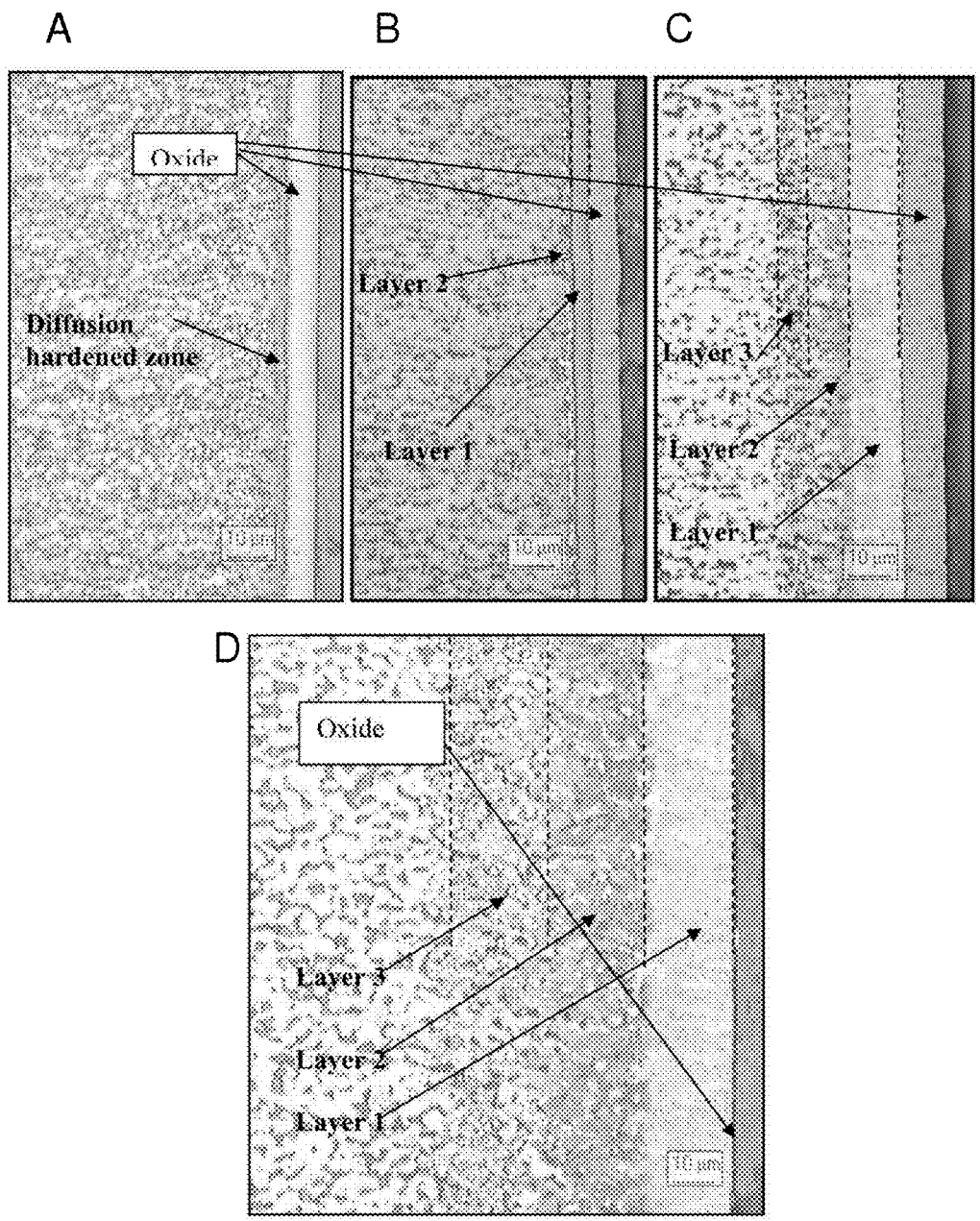
FIG. 12 shows cross-sectional metallographic images; (a) Davidson-type oxidized zirconium composition, (b) oxidized at 635° C. for 75 minutes and diffusion hardened at 585° C. for 10 hours, (c) oxidized at 690° C. for 60 minutes and diffusion hardened at 685° C. for 20 hours, and (d) oxidized at 635° C. for 75 minutes and diffusion hardened at 750° C. for 20 hours. The dotted lines on the images show the demarcation of layers.

Although most of the discussion relates to oxidize ceramic compositions, the present invention encompasses both ceramic compositions also (these include oxides, nitrides, borides, carbides, and any combination of the foregoing). The ceramic composition of the present invention has a substantially thicker diffusion hardened zone than the Davidson-type oxidized zirconium compositions. The diffusion zone of the compositions of the present invention has a layered structure unlike the diffusion zone of the Davidson-type compositions of the prior art. The thickness of the diffusion zone is at least equal to that of the ceramic layer formed on the surface of such an implant. This is accomplished by application of specific processes and the formation of a novel composition. FIG. 10 shows a comparison of oxygen concentration profile of the diffusion zone of Davidson-type oxidized zirconium composition and that of a composition of the present invention. The oxygen rich diffusion zone in Davidson-type oxidized zirconium composition is between 1 to 2 microns. The oxygen concentration at the interface (between the oxide and diffusion hardened zone) is approximately equal to the solubility limit of oxygen in alpha zirconium which is approximately 9% (w/w) or 30 atomic %. In the compositions shown in FIG. 10, the oxygen rich diffusion zone is greater than 15 microns. FIG. 11 shows a comparison of micro-hardness profiles of the Davidson-type oxidized zirconium composition to one of the compositions of the present invention. The depth of hardening is significantly greater in the composition of the present invention compared to the Davidson-type composition. Two profiles (585° C.-10 hours and 685° C.-10 hours) appear to follow an exponential, error function type of profile. Samples diffusion hardened at 750° C. appear to follow a combination of uniform and error/exponential function. These combinations of different functions appear to originate from the layered microstructure of the diffusion hardened zone and are related to the thickness of oxide retained on the surface. FIG. 12 shows anodized metallographic cross-sectional images of the Davidson-type oxidized zirconium compositions and new diffusion hardened compositions of the present invention. FIG. 12 (a) shows the Davidson-type oxidized zirconium composition. It is characterized by the oxide and a very small unresolved diffusion hardened zone. The layered structure of the diffusion hardened zone of the present invention is absent in the Davidson-type composition. The total hardening depth of this composition is approximately 7 microns. FIG. 12 (b) illustrates the composition of the present invention. This particular composition has zirconium oxide and the diffusion zone that is characterized by at least two layers. The first layer is beneath the oxide and the second layer is beneath the first layer. Thickness of the second layer is less than the first layer. The total hardening depth is approximately 12 microns.

Figure 13:
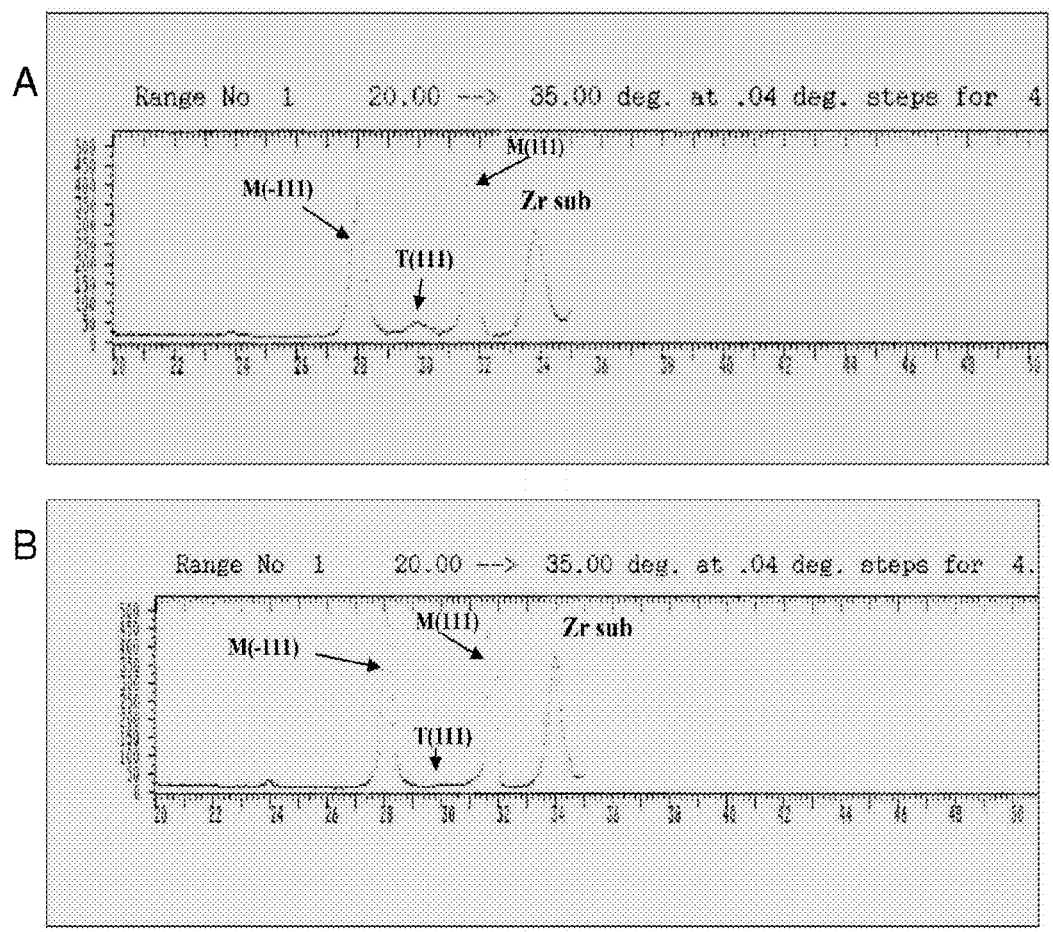
FIG. 13 shows XRD pattern of (a) Davidson-type oxidized zirconium and (b) one of the compositions of this invention. The M(−111) and M(111) are from −111 and 111 plane, T(111) is from tetragonal 111 plane. The T(111) peak for new composition is negligible indicating smaller tetragonal phase in the oxide compared to the oxide of Davidson-type oxidized zirconium. The monoclinic phase analysis was carried using ASTM F 1873.

FIG. 12 (c) shows another embodiment of the composition of the present invention. This particular composition has zirconium oxide on the surface and the diffusion zone that is characterized by at least three layers. The first layer is beneath the oxide, the second layer is beneath the first layer and the third layer is beneath the second layer. The thickness of the first layer is greater than the second layer and the thickness of the second layer is greater than that of the third layer. The total hardening depth is approximately 30 microns. FIG. 12 (d) shows another embodiment of the composition of the present invention. This particular composition has zirconium oxide layer thickness which is less than 0.2 microns and difficult to resolve under an optical microscope. The first layer is beneath the thin oxide. The second layer is beneath the first layer and the third layer is beneath the second layer. All the layers in this particular composition have similar thicknesses. In one aspect of this invention, the oxide is preferentially retained on the surface (FIGS. 12(b), 12(c) and 12(d)) during the vacuum treatment. This particular aspect leads to further distinctions between the Davidson-type oxidized zirconium composition and that of the present invention. The monoclinic content of the composition disclosed in this invention is typically greater than 96% (v/v). The typical monoclinic content of the Davidson-type oxidized zirconium composition is less than 93% (v/v) (V. Benezra, S. Mangin, M. Treska, M. Spector, G. Hunter and L. Hobbs, Materials Research Society Symposium Proceedings, Volume 550, Symposium held Nov. 30-Dec. 1, 1998, Boston, Mass., USA, L. Hobbs, V. Benezra Rosen, S. Mangin, M. Treska and G. Hunter, International Journal of Applied Ceramic Technology, 2(3), 221-246, 2005 and Sprague, J., Aldinger, P., Tsai, S., Hunter, G., Thomas, R., and Salehi, A., "Mechanical behavior of zirconia, alumina, and oxidized zirconium modular heads", ISTA 2003, vol. 2, S. Brown, I. C. Clarke, and A. Gustafson (eds.), International Society for Technology in Arthroplasty, Birmingham, Ala., 2003.). FIG. 13 shows the X-ray diffraction pattern of a Davidson-type oxidized zirconium and the X-ray diffraction pattern of the composition of the present invention. The reflection of tetragonal phase is prominently present in Davidson-type composition whereas it is negligibly small in the composition disclosed in this invention. The typical monoclinic content of the composition of the present invention is equal to or greater than 96% (see Table 1). The Davidson-type oxidized zirconium was produced by oxidizing at 635° C. for 75 minutes. One embodiment of the composition of the present invention was produced by oxidizing at 635° C. for 150 minutes and vacuum diffusion hardening at 685° C. for 10 hours at $10^{-4}$ torr. The oxide was retained at the end of the process. The metallic hardened layer and part of the oxide were removed by mechanical polishing prior to x-ray diffraction analysis. The remaining phases are most likely cubic or tetragonal or amorphous or a combination thereof.

TABLE 1

Percent monoclinic content analysis of Davidson-type oxidized zirconium and one of the compositions disclosed in this invention.

| Sample | Davidson-type oxidized zirconium | Composition of the present invention |
|---|---|---|
| 1 | 84 ± 2 | 97 ± 1 |
| 2 | 82 ± 1 | 98 ± 2 |
| 3 | 82 ± 1 | 98 ± 1 |

TABLE 1-continued

Percent monoclinic content analysis of Davidson-type oxidized zirconium and one of the compositions disclosed in this invention.

| Sample | Davidson-type oxidized zirconium | Composition of the present invention |
|---|---|---|
| Hobbs et. al. | <93 | — |
| Sprague et. al. | 88 ± 3 | — |

Figure 14:
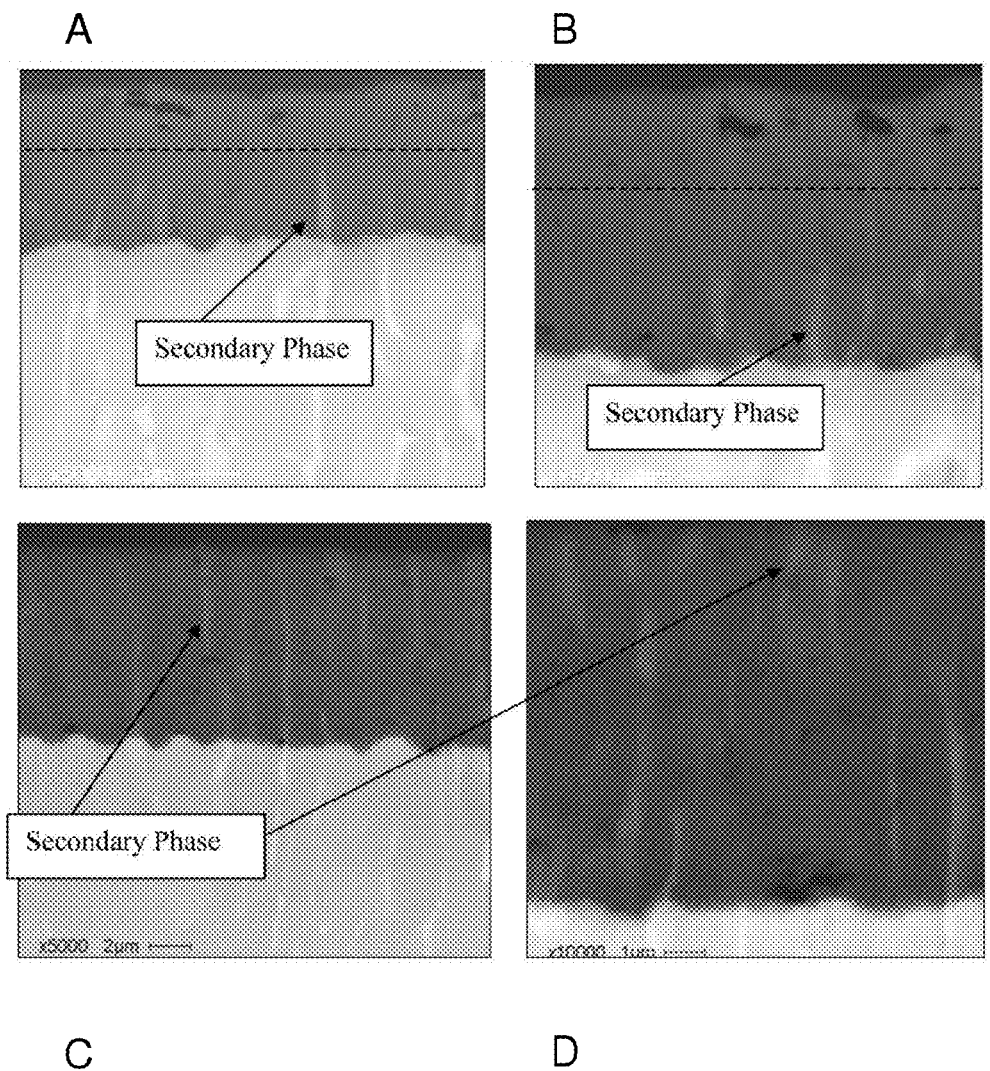
FIGS. 14 (a) and (b) show a Davidson-type oxidized zirconium composition; (c) and (d) show one of the compositions of this invention. The sample shown in (c) and (d) was oxidized at 690° C. for 60 minutes and diffusion hardened at 685° C. for 20 hours. The oxide was retained on the surface. This is a longitudinal cross-section of the sample. The orientation of secondary phase is different in transverse section. A dotted line is drawn to show how far the secondary phase is present in the oxide. The samples are imaged using back scattered electron mode with accelerating voltage of 20 kV.
Figure 15:
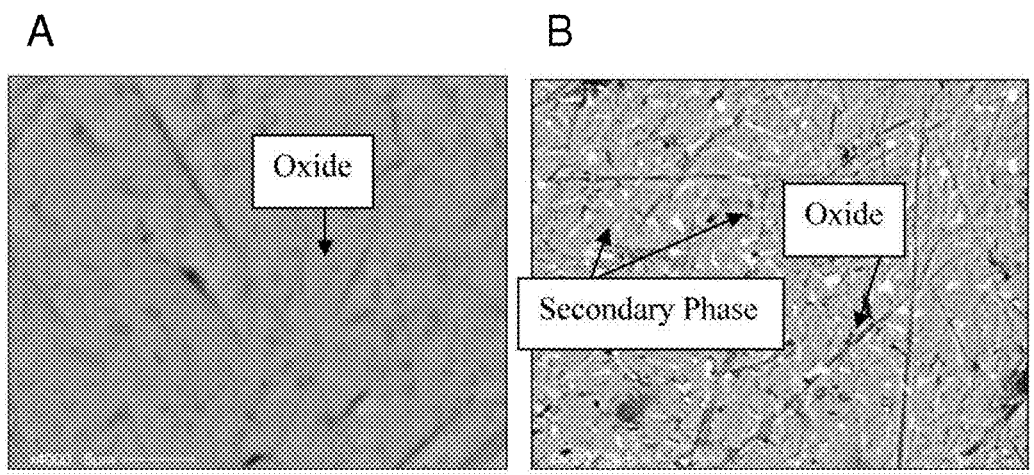
FIG. 15 illustrates (a) an oxide of Davidson-type oxidized zirconium composition, and (b) an oxide of the present invention. The bright white areas in image (b) are secondary phase.

At room temperature, zirconium oxide is stable as a monoclinic phase. It is believed that the prolonged treatment at elevated temperature led to this distinction between the two compositions. Another distinction in composition between the Davidson-type composition and that of the present invention is the structure of ceramic layer. In the Davidson-type oxidized composition a distinct secondary phase is seen in the vicinity of the interface between the oxide and the substrate. This secondary phase extends from the substrate through the interface into the oxide. This phase penetrates to an extent of approximately $3/4^{th}$ or less of the oxide thickness. Only in rare occasions, this phase is seen at the outer surface of the Davidson-type oxidized zirconium composition. In contrast to the Davidson-type oxidized composition, the composition of present invention shows this distinct secondary phase through the entire thickness of the ceramic layer. In the Davidson-type oxidized composition, this distinct secondary phase is visible only up to a certain depth in the oxide from the oxide-metal interface. FIG. 14 shows scanning electron microscope images of the cross-section showing oxide of Davidson-type oxidized zirconium composition and that of the present invention. In the Davidson-type composition of zirconium oxide, the secondary phase is present from the oxide/metal interface to at most $3/4^{th}$ of the oxide thickness (FIGS. 14 (a) and 14 (b)). Occasionally it is seen on the surface of the oxide. This is consistent with that reported by Benezra et. al. and Hobbs et. al. Whereas, in the composition of the present invention, secondary phase is present through the entire thickness of the oxide (FIGS. 14 (c) and 14(d)). Although not intending to be bound by theory, it is believed that this is due to the prolonged vacuum treatment. FIG. 15 shows scanning electron microscope images of the surface of the oxide. No secondary phase is seen on surface of Davidson-type oxidized zirconium composition (FIG. 15 (a)). The composition disclosed in this invention clearly shows presence of secondary phase on the surface (FIG. 15 (b)). It should be noted that this distinction is visible when the ceramic layer is retained on the surface at the end of the vacuum treatment. If re-formation of the ceramic layer is carried out after the diffusion treatment secondary phase may not be present up to the surface. As stated previously, underneath the ceramic layer is a layered structure of diffusion zone. The Zr-2.5Nb is comprised of two phases, alpha (hexagonal) and beta (cubic). The diffusion zone is predominantly alpha phase (hexagonal). A minor amount of beta (cubic) phase (less than 7% (v/v)) can be present in the first layer of diffusion zone. The first layer is predominantly alpha phase and the volume fraction of beta phase gradually increases in the diffusion layer towards the substrate. If the zirconium alloy is predominantly single phase (alpha) then the beta phase in the diffusion zone will be significantly less than it is in the substrate.

Figure 16:
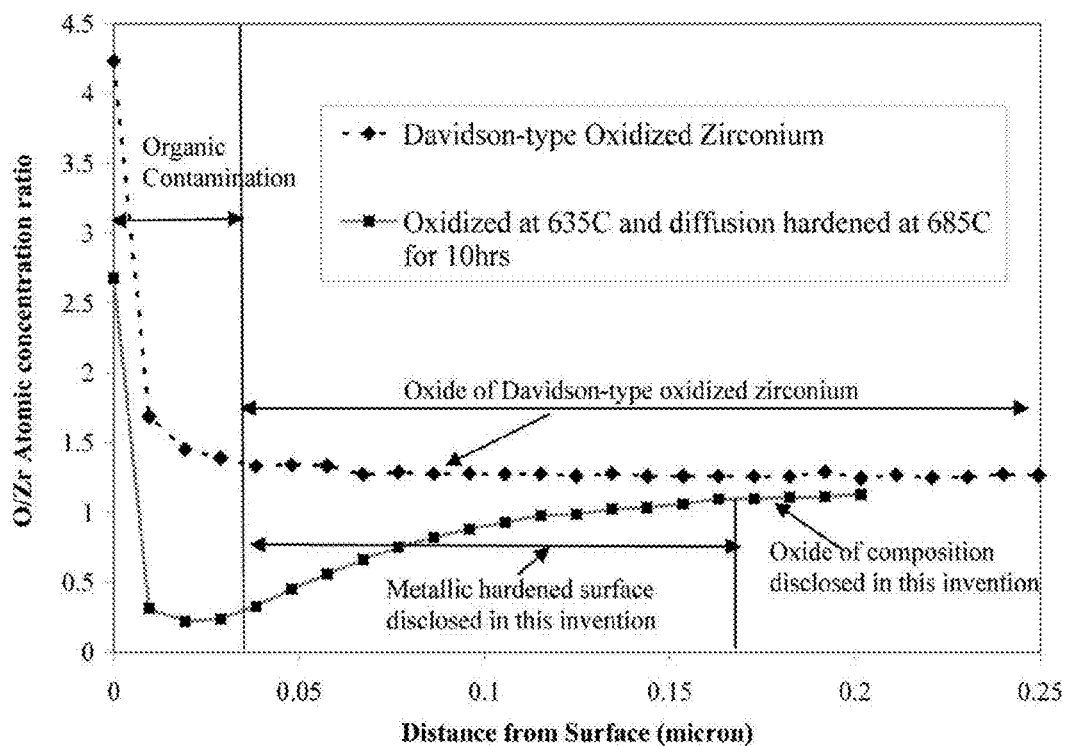
FIG. 16 shows the ratio of atomic concentration of oxygen to atomic concentration of zirconium of Davidson-type oxidized zirconium composition and that disclosed in this invention. The depth profile analysis was carried out using x-ray photoelectron spectroscope (Al kα, take off angle 45°) and an ion gun for sputtering (Ar+, 3 keV, silica sputter rate of 48 angstroms/minute).

In one embodiment of the composition of the present invention, when the ceramic layer is retained on the surface during the vacuum treatment, based on the pressure and temperature used, metallic hardened surface is formed on the ceramic layer along with the diffusion zone formed underneath the ceramic layer. This metallic hardened zone is the result of the reaction at the ceramic layer/vacuum interface. FIG. 16 shows ratio of atomic concentration of oxygen to atomic concentration of zirconium (O/Zr) of Davidson-type oxidized zirconium composition and one of the compositions disclosed in this invention. If the organic contamination on the surface is ignored, the O/Zr ratio of Davidson-type composition starts at 1.4 and seems to be constant through the thickness evaluated in this analysis. For the new composition disclosed in this invention, O/Zr ratio starts at 0.3 and gradually increases to 1.2 in the oxide. The top 0.2 micron layer shown in the image is the metallic hardened layer described in this invention. This layer may or may not be retained on the final medical implant. Below this metallic hardened layer is the ceramic layer (in this case, an oxide) and below the oxide is the layered structure of diffusion zone. The composition of the oxide disclosed in this invention appears to be slightly more oxygen deficient compared to the Davidson-type composition. It should be noted that this analysis was carried out using x-ray photoelectron spectroscope (XPS). The surface was analyzed while being removed (sputtered) using an ion gun. The depths are approximate and are based on the sputtering rate of silicon dioxide. XPS is sensitive to surface organic contamination (carbon-oxygen) and hence shows higher O/Zr ratio on the surface. It is reasonable to surmise that the top few layers (0.03 micron) are the surface contaminants.

The diffusion-hardened ceramic layers of this invention are produced by employing three processes. All processes can be performed in a single or multiple steps. The processes are (1) ceramic layer formation (i.e., oxidation, nitridation, boridation, carburization, or any combination thereof), (2) diffusion hardening, and optionally, (3) ceramic layer formation. If the ceramic layer is retained on the surface during diffusion hardening, process 1 and 2 may be sufficient. If the final application is such that a ceramic layer is not required on the surface, a temperature and time can be chosen in such a way that process 2 will dissolve the ceramic layer completely. Alternatively, the surface ceramic layer may be removed by mechanical, chemical or electrochemical means. When the ceramic layer is retained on the surface it may form a metallic hardened layer on the oxide. This film may or may not be removed for the final product. If the ceramic layer is completely dissolved into the substrate and re-formation of the ceramic layer is desired then a diffusion profile is obtained which will produce a high integrity and defect-free ceramic layer during the ceramic layer formation process. This diffusion profile can be an exponential function, an error function, a uniform, or any sequential combination thereof (FIG. 6, Profiles 1 to 3). It should be noted that some of these functions may also be attributed to be linear or higher order polynomials. It should be noted that the combination of diffusion profile and retained oxide is obtained through careful control of time, temperature and pressure during the ceramic layer formation process and the diffusion hardening process.

For Zr—Nb-based alloys, the damage-resistant implant is such that it has ceramic layer thicknesses ranging from 0.1 to 25 microns and a diffusion hardened zone (DHZ) significantly greater than 2 micron. The DHZ can be 70 micron or greater. The DHZ is defined as the region which has hardness at least 1.1 times of the substrate hardness.

There are three general methods to produce the composition of the present invention. It should be understood that variations by way of substitutions and alterations from these general methods which do not depart from the spirit and scope of the invention are understood to be within the scope of the invention. In this way, the general methods described below are merely illustrative and not exhaustive. In each of the examples provided, the ceramic layer formation steps are oxidation steps (thereby producing ceramic oxides). It should be understood that these steps are not limited to oxidation and the formation of ceramic oxides; in addition to or in the alternative of, an oxidation step, one may use a carburization step, a boridation step, a nitridation step, or any combination thereof (including a combination of oxidation and one or more other steps). In this way, the ceramic so produced can be any one or, or a combination of an oxide, nitride, boride, and carbide.

In Method A, the ceramic oxide and a thick diffusion hardened zone on the damage-resistant surface is formed by carrying the following process steps:

1. Ceramic Layer Formation. Oxidation by diffusion of oxygen in air at temperature less than 700° C. for times greater than 5 minutes. The oxidation time can be approximated by parabolic relationship of time and oxide thickness ($x^2$=kt, where k is a constant, t is time and x is thickness of the oxide. k is function of temperature). In certain cases a cubic or higher order polynomial relationship may also be employed.

Figure 17:
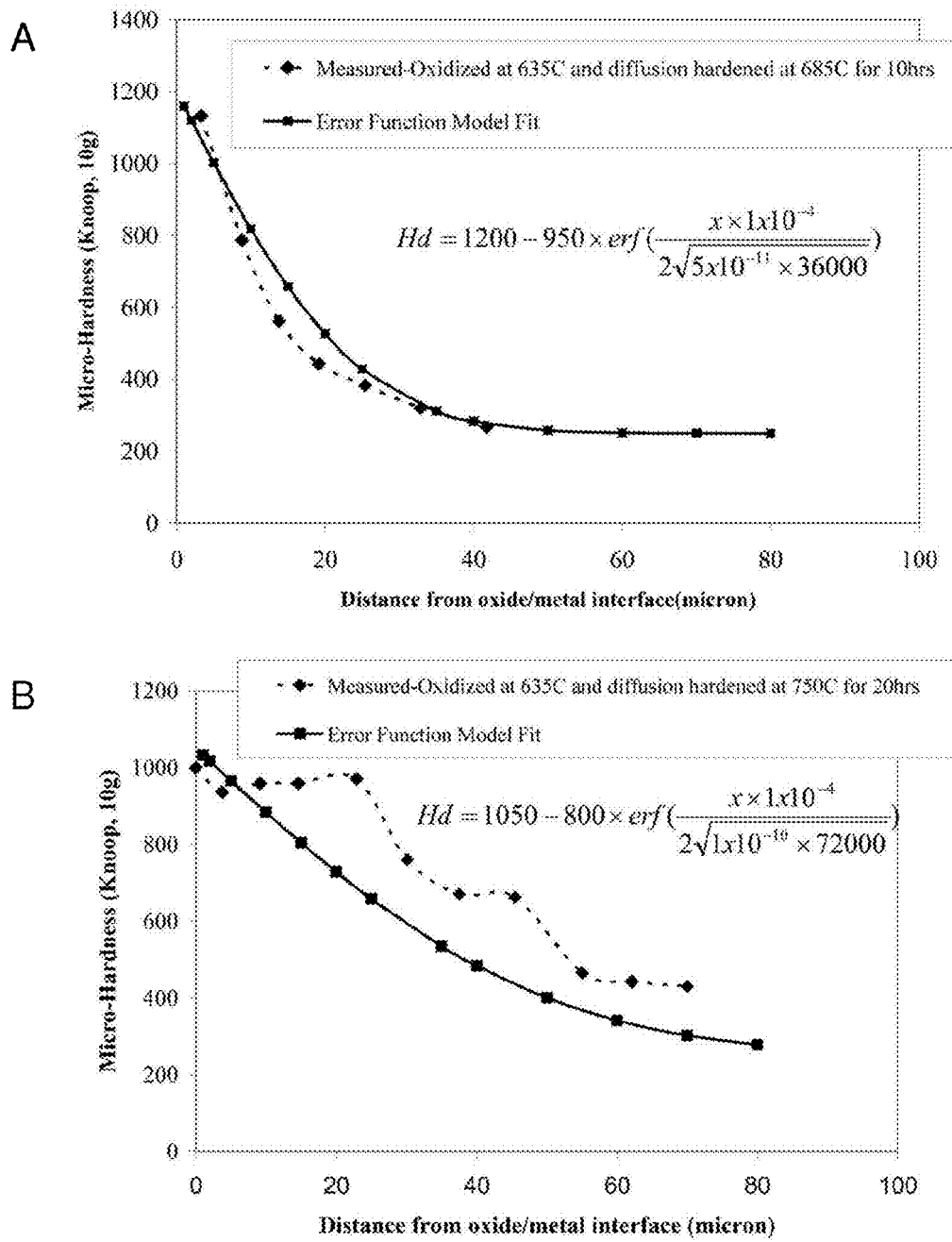
FIG. 17 illustrates an error function fit to the micro-hardness indents in the diffusion hardened zone to estimate the depth of hardening. The diffusivity values are in $cm^2/s$ and are approximate. Time is in seconds and distance is in microns.

2. Diffusion Hardening. Treating under vacuum or under inert gas the above said implant at a temperature range from 500° C. to 1000° C. for a period of greater than 1 hour in vacuum at a pressure less than atmospheric (typically less than $10^{-2}$ ton). This step either partially or completely dissolves the oxide layer formed in step 1. The oxygen atoms thus released are driven deeper into the alloy substrate, hardening the material. The time and temperature required to obtain a certain diffusion hardening depth can be estimated from an error-function relationship. Hardness at depth d ($H_d$) is given by:

$$H_d = H_i + (H_i - H_o)\mathrm{erf}\left[\frac{-d}{2\sqrt{Dt}}\right]$$

where, $H_i$ is the hardness at the interface, $H_o$ is the hardness of the bulk substrate significantly away from the diffusion zone, D is diffusivity of diffusing species at the vacuum treatment temperature and t is time of treatment. "erf" is the error function. All the parameters should be used in consistent units. The diffusivity of oxygen can be obtained from the published literature. In this relationship, it is assumed that the hardness is directly proportional to oxygen at all concentration levels, and diffusivity of diffusing specie is independent of concentration. This is a simplistic view to approximately estimate the depth of hardening. Those skilled in the art can hypothesize different relationships of diffusing specie and the hardness and may obtain a different relationship but the overall shape and profile will follow that described in this invention. As an example, if the relationship is exponential or combination of uniform and exponential or error function, then the depth estimation will be inaccurate using the above said equation. An example of same is shown in FIG. 17. Sample in FIG. 17 (*a*) was oxidized at 635° C. for 75 minutes and then subsequently diffusion hardened at 685° C. for 10 hrs. The oxide was retained on this sample after the vacuum diffusion treatment. An error function fit seems to be adequate. Sample in FIG. 17 (*b*) was oxidized at 635° C. for 75 minutes and then was diffusion hardened at 750° C. for 20 hrs. A very small fraction of oxide was retained on the surface. An error function fit is not adequate for this particular sample. It seems that sequential combination of error function and uniform fit may model the hardening behavior.

3. Optional Ceramic Layer Formation. Optionally, the implant is subsequently oxidized again at temperature less than 700° C. in air for times greater than 5 minutes. As shown in FIGS. 6 and 7, a suitable hardness profile prior to oxidation is essential to produce high integrity substantially defect-free oxide.

Figure 18:
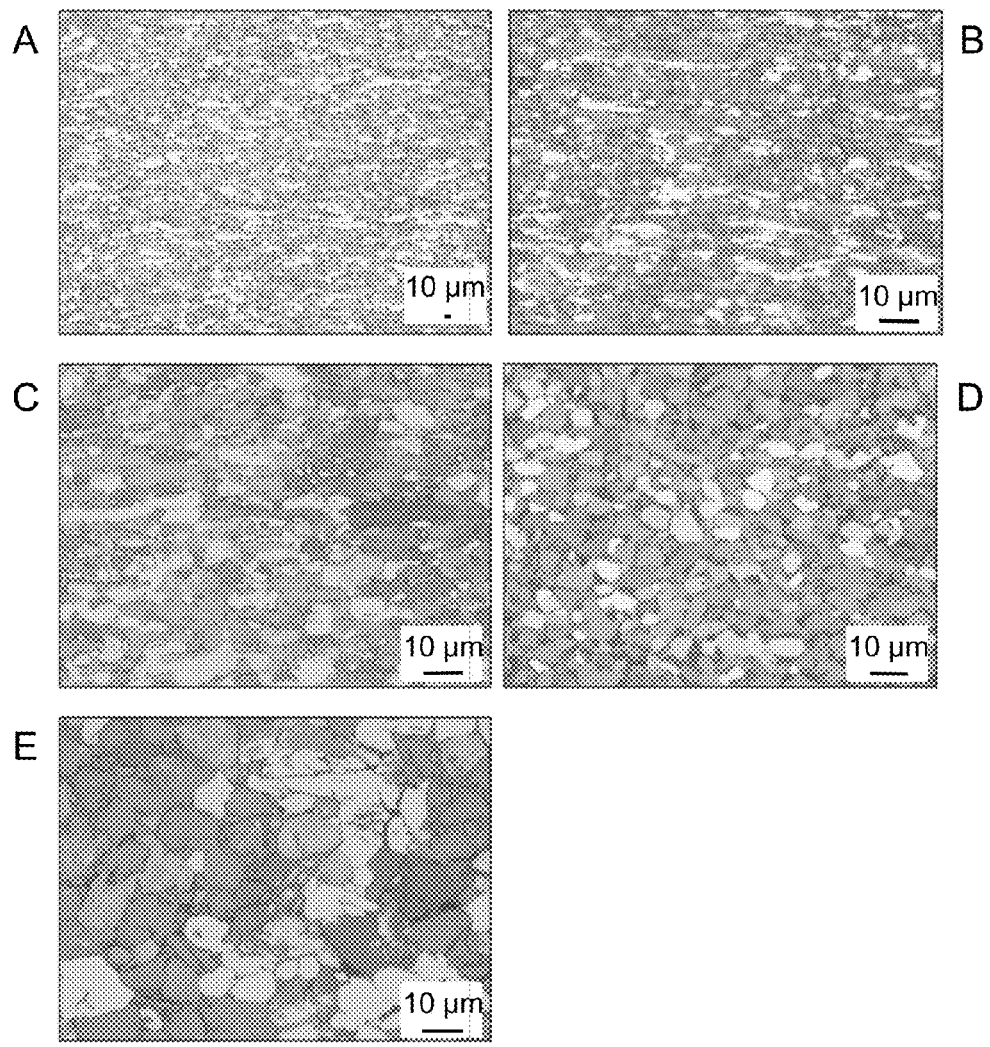
FIG. 18 illustrates the microstructure of (a) as received Zr-2.5Nb bar stock, (b) oxidized at 635° C. for 75 minutes and diffusion hardened at 585° C. for 10 hours, (c) oxidized at 690° C. for 60 minutes and diffusion hardened at 685° C. for 20 hours, and (d) oxidized at 635° C. for 75 minutes and diffusion hardened at 750° C. for 20 hours, and (e) oxidized at 850° C. for 20 minutes and diffusion hardened at 850° C. for 22 hours. The samples were polished using standard metallographic techniques and were heat tinted to reveal the grain size.

Ceramic layer formation and diffusion hardening at temperatures less than 700° C. helps to preserve the microstructure of the substrate. FIG. 18 shows the substrate microstructure of samples diffusion hardened at different temperatures. The grain size of the as-received bar stock is less than 1 micron (FIG. 18 (*a*)). The microstructure shows orientation of the grains along the rolling direction. The grain size of the samples diffusion hardened at 585° C. show slight coarsening (FIG. 18 (*b*)). The orientation of the microstructure is still preserved. FIG. 18 (*c*) shows grain size of the sample diffusion hardened at 685° C. for 20 hours. The grain size shows noticeable coarsening compared to as-received bar stock. The orientation of the grains is still present. FIG. 18 (*d*) shows microstructure of samples diffusion hardened at 750° C. for 20 hours. There is significant coarsening of the grains. The orientation of the grains has disappeared and the grains have become equiaxed. The size of the grains is greater than 1 micron. FIG. 18 (*e*) shows microstructure of samples diffusion hardened at 850° C. for 22 hours. Significant coarsening of the grains can be seen. The size of the grains is above 10 microns. Alternatively, the second step may be carried out at a temperature and time such that part of the oxide formed in step 1 is retained on the surface. The third step of ceramic layer formation may be altogether eliminated if any remaining ceramic layer is sufficient. It should be noted that when the ceramic layer is retained on the surface, a thin metallic hardened film forms on the surface. The composition of the film is shown FIG. 16. This film may be retained on the surface or can be polished by mechanical, chemical or electrochemical means if desired. Alternatively, the second step of diffusion hardening is carried out in an inert atmosphere such as composed of argon (or other inert gas) with partial pressure of oxygen (or other diffusion hardening species) in the system typically less than $0.2 \times 10^{-2}$ ton and temperature range from 500° C. to greater than 800° C. Alternatively, if re-formation of ceramic layer is desired as a third step, an adequate diffusion profile is obtained to produce a high integrity, predominantly defect-free ceramic layer (FIGS. 6 and 7).

In Method B, the ceramic oxide and a thick diffusion hardened zone on the damage-resistant surface is formed by carrying the following process steps:

1. Ceramic Layer Formation. Oxidation by diffusion of oxygen in air at temperature range of 500° C. to 1000° C. (preferably less than 700° C.) for times greater than 5 minutes. The oxidation time can be approximated by parabolic relationship of time and oxide thickness ($x^2$=kt, where k is a constant, t is time and x is thickness of the oxide. k is function of temperature). In certain cases a cubic or higher order polynomial relationship may also be employed.

2. Diffusion Hardening. Treating under vacuum (i.e., pressure less than about $10^{-2}$ ton) or under inert gas the above said implant at a temperature of less than 700° C. The exact temperature and time are chosen such that a desired oxide thickness remains on the surface after the vacuum treatment step is completed. This step likely partially consumes the oxide layer formed in step 1. The oxygen atoms thus released are driven deeper into the alloy substrate, hardening the material. The diffusion hardening depth can be estimated from an error-function relationship. Hardness at depth d ($H_d$) is given by:

$$H_d = H_i + (H_i - H_o)\text{erf}\left[\frac{-d}{2\sqrt{Dt}}\right]$$

where, $H_i$ is the hardness at the interface, $H_o$ is the hardness of the bulk substrate significantly away from the diffusion zone, D is diffusivity of diffusing species and t is time of treatment. "erf" is the error function. All the parameters should be used in consistent units. The diffusivity of oxygen can be obtained from the published literature. In this relationship, it is assumed that the hardness is directly proportional to oxygen at all concentration levels, and diffusivity of diffusing specie is independent of concentration. This is a simplistic view to approximately estimate the depth of the hardening. Those skilled in the art can hypothesize different relationships of diffusing specie and the hardness and may obtain a different relationship but the overall shape and profile will follow that described in this invention. It should be noted that this relationship is an approximate way to estimate the depth of hardening. If the profile is exponential or combination of uniform and exponential or error function, then the depth estimation using the equation above will be inaccurate. An example of same is shown in FIG. 17. Sample shown in FIG. 17 (a) was oxidized at 635° C. for 75 minutes and then subsequently diffusion hardened at 685° C. for 10 hours. Oxide was retained on the surface. An error function fit seems to be adequate. Sample in FIG. 17 (b) was oxidized at 635° C. for 75 minutes and then was diffusion hardened at 750° C. for 20 hours. A small fraction of oxide was retained on the surface. An error function fit is not adequate for this particular sample. It seems that sequential combination of error function and uniform fit may model the hardening behavior.

3. Optional Ceramic Layer Formation. Optionally, the implant is subsequently oxidized again at temperature less than 700° C. in air for times greater than 5 minutes. As shown in FIGS. 6 and 7, a suitable hardness profile prior to oxidation is essential to produce high integrity substantially defect-free oxide.

By vacuum (or inert gas) treating at lower temperatures a desired oxide thickness remains on the surface and promotes the preservation of the microstructure of the substrate. FIG. 18 shows the substrate microstructure of samples diffusion hardened at different temperatures. The grain size of the as-received bar stock is less than 1 micron (FIG. 18 (a)). The microstructure shows orientation of the grains along the rolling direction. The grain size of the samples diffusion hardened at 585° C. show slight coarsening (FIG. 18 (b)). The orientation of the microstructure is still preserved. FIG. 18 (c) shows grain size of the sample diffusion hardened at 685° C. for 20 hours. The grain size shows noticeable coarsening compared to as-received bar stock. The orientation of the grains is still present. FIG. 18 (d) shows microstructure of samples diffusion hardened at 750° C. for 20 hours. There is significant coarsening of the grains. The orientation of the grains has disappeared and the grains have become equiaxed. The size of the grains is greater than 1 micron. FIG. 18 (e) shows microstructure of samples diffusion hardened at 850° C. for 22 hours. Significant coarsening of the grains can be seen. The size of the grains is above 10 microns. Alternatively, if re-formation of ceramic layer is desired as a third step, an adequate diffusion profile is obtained to produce a high integrity, predominantly defect-free ceramic layer (FIGS. 6 and 7).

In Method C, the ceramic oxide and a thick diffusion hardened zone on the damage-resistant surface is formed by carrying the following process steps:

1. Ceramic Layer Formation. Oxidation by diffusion of oxygen in air at temperature less than 700° C. for times greater than 5 minutes. The oxidation time can be decided based on the parabolic relationship of time and oxide thickness ($x^2$=kt, where k is a constant, t is time and x is thickness of the oxide. k is function of temperature). In certain cases a cubic relationship may also be employed.

2. Diffusion Hardening. Treating under vacuum (i.e., pressure less than about $10^{-2}$ ton) or under inert gas the above said implant at a temperature of less than 700° C. The exact temperature and time is chosen such that a desired oxide thickness remains on the surface after the vacuum treatment step is completed. This step likely partially consumes the oxide layer formed in step 1. The oxygen atoms thus released are driven deeper into the alloy substrate, hardening the material. The time and temperature required to obtain a certain diffusion hardening depth can be estimated from an error-function relationship. Hardness at depth d ($H_d$) is given by:

$$H_d = H_i + (H_i - H_o)\text{erf}\left[\frac{-d}{2\sqrt{Dt}}\right]$$

where, $H_i$ is the hardness at the interface, $H_o$ is the hardness of the bulk substrate significantly away from the diffusion zone, D is diffusivity of diffusing species and t is time of treatment. "erf" is the error function. All parameters should be used in consistent units. The diffusivity of oxygen can be obtained from the published literature. In this relationship, it is assumed that the hardness is directly proportional to oxygen at all concentration levels, and diffusivity of diffusing specie is independent of concentration. This is a simplistic view to approximately estimate the depth of hardening. As an example, if the relationship is exponential or combination of uniform and exponential or error function, then the depth estimation will be inaccurate. An example of same is shown in FIG. 17. Sample in FIG. 17 (a) was oxidized at 635° C. for 75 minutes and then subsequently diffusion hardened at 685° C. for 10 hours. Oxide was retained on the surface. An error function fit seems to be adequate. Sample in FIG. 17 (b) was oxidized at 635° C. for 75 minutes and then was diffusion hardened at 750° C. for 20 hours. A small fraction of oxide was retained on the surface. An error function fit is not adequate for this particular sample. It seems that a sequential combination of error function and uniform fit may model the hardening behavior.

3. Optional Ceramic Layer Formation. Optionally, the implant is subsequently oxidized again at temperature less than 700° C. in air for times greater than 5 minutes. As shown in FIGS. 6 and 7, a suitable hardness profile prior to oxidation is essential to produce high integrity, substantially defect-free oxide.

By performing the ceramic layer formation and diffusion hardening (vacuum or inert gas treatment) steps at lower temperatures preservation of the microstructure of the substrate is achieved and a desired ceramic layer thickness remains on the surface as shown in FIGS. 12 and 18. The combination of the ceramic layer formation and diffusion hardening steps described results in a significantly thicker diffusion hardened zone (greater than 2 microns and preferably greater than 5 microns) in comparison to Davidson-type diffusion hardened oxide and/or nitride compositions. Additionally, the totality of the ceramic layer and the diffusion hardened zone is 5 microns or greater. These properties result in a more damage resistant and wear resistant surface, among other advantages. The properties of the new composition makes it applicable to hard-on-hard medical implant applications. Non-limiting examples of such include knee and hip prostheses having one surface of the new composition articulating against another surface of the new composition.

It should be understood that the temperature and time parameters can be varied from those provided above, particularly in the case of different substrate compositions. Additionally, the processes may be carried out in a controlled atmosphere. Illustrative but non-limiting examples of a controlled atmosphere include, controlled oxygen and nitrogen partial pressure, oxygen plasma, in the presence of water gas reactions, in the presence of reactive gases such as oxygen and ozone in the presence of inert gases such as argon and nitrogen, in the presence of oxidizing or reducing salts, in the presence of glasses etc. Examples of inert gases include nitrogen, argon, etc. Examples of reactive gases include hydrogen, methane, other hydrocarbons, etc. Other controlled atmosphere conditions, known to those of skill in the art are also included. The goal is to form the composition under conditions that do not significantly change the microstructure of the substrate alloy.

Alternatively, the process of ceramic layer formation and diffusion hardening can be carried out in an atmosphere that is lean in oxygen (or other ceramic forming species) content (e.g., partial pressure of oxygen less than 0.05 bar). Alternatively, the process can be carried out in a single step comprising of all the above steps in one process. Alternatively, the process can be carried out in ozone atmosphere or an atmosphere whose oxidation potential is controlled by water-gas reaction such as $CO_2 + H_2 = H_2O + CO$ or using controlled moisture in an inert gases such as but not limited to helium, nitrogen, argon and krypton.

Alternatively, the ceramic layer formation and diffusion hardening can be carried out in two steps that do not change microstructure of the substrate alloy significantly. The process of ceramic layer formation and diffusion hardening can be carried out in a two step process. In the first step, the alloy is treated with ceramic forming species at a temperature above 700° C. for a period of greater than 12 hours that forms a thicker diffusion zone along with a cracked ceramic layer or the alloy is diffusion hardened as described in methods A, B and C. In a second step, the ceramic layer or part of the diffusion zone is removed by mechanical, chemical or electrochemical means and the alloy is subsequently treated to form a ceramic layer at a lower temperature and time to form an adherent ceramic layer with an already formed diffusion zone and thus producing the damaged resistant implant.

Alternatively, the substrate material is first diffusion hardened using a lean concentration of diffusion hardening species and then a ceramic layer is formed (using a more concentrated dose of ceramic-forming species to form the ceramic layer).

A two step process can be used. In the first step the material is diffusion-hardened (oxygen, carbon, boron, or nitrogen) in controlled conditions in which the partial pressure of the hardening species are lean enough not to form stable ceramic compounds with the alloy. The diffusion zones can be controlled as described above. This is followed by oxidation, carburization, nitridation, borization or any combination thereof as described above.

The damage-resistant implant is produced by forming the ceramic layer at a temperature preferably ranging from 500° C. to greater than 1000° C. for a time preferably ranging from 5 minutes to greater than 6 hours. It is preferred that the ceramic formation temperature be under 700° C. to promote preservation of the substrate microstructure. The time and temperature may be determined from the Arrhenius and parabolic relationship amongst the ceramic layer thickness, diffusion-hardened zone thickness, and temperature. Vacuum or inert gas treatment (diffusion hardening) is preferably performed at a temperature preferably ranging from 500° C. to greater than 1000° C. for a time preferably ranging from 15 minutes to greater than 30 hours. It is preferred that the diffusion hardening treatment temperature be under 700° C. to preferentially preserve any of the ceramic oxide formed in step 1 and also to promote preservation of the substrate microstructure. An optional step of re-formation of ceramic layer may be performed after the initial ceramic layer formation step if additional ceramic layer growth is desired.

The resulting surface composition can be subject to a variety of surface preparation techniques after the step of diffusion-hardening to form the adherent oxide. Such techniques include, but are not limited to, those techniques known in the art to be applicable to diffusion-hardened surfaces. It is expected that other, more rigorous techniques are applicable to the composition of the present invention due to its greater degree of damage resistance.

In the composition used in the medical implant of the present invention, the totality of the thickness of the ceramic layer and the diffusion hardened zone is greater than 5 microns, and preferably greater than 10 microns. Because the ceramic layer may or may not be present (it can range in thickness from 0 to 25 microns), this requirement may be met by a diffusion hardened zone of a thickness of greater than 5 microns (and preferably greater than 10 microns) with no ceramic layer above it or an infinitesimally small ceramic layer above it. Where both layers are present, the ceramic layer is on the surface and is above the diffusion hardened zone. While the diffusion hardened zone is one of the two aforementioned layers, the diffusion hardened zone itself consists of at least two distinct layers layer (visible by metallographic analysis). The first layer of the diffusion hardened zone has a relatively high concentration of diffusion hardening species (higher than that of the bulk substrate zirconium or zirconium alloy) and may be saturated with the diffusion hardening species. The zirconium in the first layer is predominantly alpha phase zirconium (the first layer of the diffusion hardened zone is that layer which is closest to the ceramic layer, or, where the ceramic layer is absent, the first layer is that layer which is nearest to the surface of the composition). The second layer is below the first layer and has a lower content of diffusion hardening species than the first layer. The diffusion hardened zone has a diffusion hardening species concentration profile such that, in one or more cross-sections of the diffusion hardened zone, the concentration of diffusion hardening species decreases as either an error function, an exponential function, a near uniform distribution, or sequential combinations thereof. Where combinations of functional profiles are referred to, it should be understood that such combinations are sequential combinations and do not refer to the superposition of the various functional profiles. Where the diffusion hardened layer is very thick due to the use of long formation times, the distribution may approach a uniform distribution in at least some sections of the diffusion hardened zone.

The layered structure of the diffusion hardened zone can be detected by metallographic analytical techniques known to those of ordinary skill in the art. These include, but are not limited to, anodization, heat tinting, x-ray diffraction, Auger spectroscopy, depth profiling, etc.

As described above, the process can be used for an extended period to form a thick cracked ceramic layer and a thick diffusion hardened layer. The cracked ceramic layer can then be removed to retain the diffusion hardened layer for subsequent re-formation of another ceramic layer.

The new composition has application in medical implants of all varieties. It is expected to be particularly beneficial for use in articulating implants, such as, but not limited to hip and knee implants. Use of such product in other biomedical applications such spinal devices, small joints, shoulder joints, etc.

Resulting medical implants comprising diffusion-hardened ceramic layers of the variety described herein are heated to desired temperatures using electric heating, radiative heating, induction heating or using techniques such as spark plasma sintering or field assisted sintering. This is accomplished by use of an alloy of Ti, Zr and Nb that is capable of producing thicker totality of hardened zones (ceramic layer and thick diffusion hardened zone) that is produced by specific processes.

The present composition will be applicable for any and all medical implants, but in particular for articulating medical implants such as, but not limited to, hip, knee, shoulder, elbow orthopedic implants, etc. Vertebral implants are also amenable to the present invention. The present invention also finds applicability to any and all non-articulating medical implants. The improved damage resistance is seen in comparison to the diffusion hardened oxides of the Davidson-type, such as those described in U.S. Pat. No. 5,037,438 to Davidson and U.S. Pat. Nos. 6,447,550; 6,585,772 and pending U.S. application Ser. No. 10/942,464 to Hunter.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of making a surface hardened medical implant comprising the steps of:

forming a medical implant of zirconium or zirconium alloy;

oxidizing or nitriding said implant at a temperature of from 500 degrees C. to 700 degrees C. to retain at least 0.1 microns of said oxide or nitride layer, to form at least 0.005 microns metallic hardened layer on top of said at least 0.1 microns thick oxide or nitride layer, and to form a diffusion zone having a thickness of at least 2 microns below said at least 0.1 microns thick oxide or nitride layer; and wherein said treating step is performed for a period of time determined based at least on a desired thickness of the diffusion zone to be formed.

2. The method of claim 1, wherein the medical implant further comprises titanium, tantalum, niobium, hafnium, and any combination thereof.

3. The method of claim 1, wherein the oxide or nitride thickness before said step of treating said implant under vacuum or inert gas is from 2 to 15 microns.

4. The method of claim 1, wherein the oxide or nitride thickness after said step of treating said implant under vacuum or inert gas is from 0.1 to 10 microns.

5. The method of claim 1, wherein the thickness of the diffusion hardened zone is from 2 to 50 microns.

6. The method of claim 1 further comprising:
removing a portion of said metallic hardened layer.

7. A method of making a surface hardened medical implant comprising the steps of:

forming a medical implant of zirconium or zirconium alloy; oxidizing or nitriding said implant at a temperature of from 500 degrees C. to 700 degrees C. to form an oxide or nitride layer having a thickness of at least 2 microns;

treating said implant under vacuum or inert gas at a temperature less than 700 degrees C. to retain at least 0.1 microns of said oxide or nitride layer, to form at least 0.005 microns metallic hardened layer on top of said at least 0.1 microns thick oxide or nitride layer, and to form a diffusion zone having a thickness of at least 2 microns below said at least 0.1 microns thick oxide or nitride layer; and polishing the metallic hardened layer with mechanical, chemical, or electromechanical devices or substances;

wherein said treating step is performed for a period of time determined based at least on a desired thickness of said oxide or nitride layer to be retained.

8. The method of claim 7, wherein the medical implant further comprises titanium, tantalum, niobium, hafnium, and any combination thereof.

9. The method of claim 7, wherein the oxide or nitride thickness before said step of treating said implant under vacuum or inert gas is from 2 to 15 microns.

10. The method of claim 7, wherein the oxide or nitride thickness after said step of treating said implant under vacuum or inert gas is from 0.1 to 10 microns.

11. The method of claim 7, wherein the thickness of the diffusion hardened zone is from 2 to 50 microns.

12. The method of claim 7 further comprising:
removing a portion of said metallic hardened layer.

* * * * *